US012649940B2

(12) United States Patent
Chen et al.

(10) Patent No.: US 12,649,940 B2
(45) Date of Patent: Jun. 9, 2026

(54) ENZYMATIC OLIGONUCLEOTIDE ASSEMBLY USING HAIRPINS AND ENZYMATIC CLEAVAGE

(71) Applicant: MICROSOFT TECHNOLOGY LICENSING, LLC, Redmond, WA (US)

(72) Inventors: Yuan-Jyue Chen, Seattle, WA (US); Bichlien Hoang Nguyen, Seattle, WA (US); Karin Strauss, Seatte, WA (US)

(73) Assignee: MICROSOFT TECHNOLOGY LICENSING, LLC, Redmond, WA (US)

( * ) Notice: Subject to any disclaimer, the term of this patent is extended or adjusted under 35 U.S.C. 154(b) by 1156 days.

(21) Appl. No.: 17/670,372

(22) Filed: Feb. 11, 2022

(65) Prior Publication Data

US 2023/0257789 A1      Aug. 17, 2023

(51) Int. Cl.

| | |
|---|---|
| *C12P 19/34* | (2006.01) |
| *B01L 3/00* | (2006.01) |
| *C07H 21/00* | (2006.01) |
| *C12N 9/00* | (2006.01) |
| *C12N 9/22* | (2006.01) |
| *C12N 9/24* | (2006.01) |
| *C12N 15/11* | (2006.01) |

(52) U.S. Cl.
CPC ......... *C12P 19/34* (2013.01); *B01L 3/502715* (2013.01); *B01L 3/502761* (2013.01); *C07H 21/00* (2013.01); *C12N 9/22* (2013.01); *C12N 9/2497* (2013.01); *C12N 9/93* (2013.01); *C12N 15/11* (2013.01); *C12Y 301/26004* (2013.01); *C12Y 302/02027* (2013.01); *C12N 2310/531* (2013.01)

(58) Field of Classification Search
CPC ........................ C12Q 1/6834; C12N 2310/531
See application file for complete search history.

(56) References Cited

U.S. PATENT DOCUMENTS

| | | | | |
|---|---|---|---|---|
| 6,017,696 A | * | 1/2000 | Heller | ................ G11C 13/0019 |
| | | | | 436/805 |
| 7,915,201 B2 | * | 3/2011 | Franch | .................... C40B 40/06 |
| | | | | 506/28 |
| 10,289,801 B2 | | 5/2019 | Church | |
| 2007/0015182 A1 | | 1/2007 | Abarzua | |
| 2013/0296194 A1 | | 11/2013 | Jacobson et al. | |
| 2015/0361422 A1 | | 12/2015 | Sampson et al. | |
| 2019/0323050 A1 | | 10/2019 | Griswold et al. | |
| 2020/0102556 A1 | | 4/2020 | Da Veiga Beltrame et al. | |
| 2020/0332341 A1 | * | 10/2020 | Tori | ........................ C12P 19/34 |
| 2021/0155923 A1 | | 5/2021 | Chen et al. | |
| 2023/0257788 A1 | | 8/2023 | Chen et al. | |
| 2024/0271171 A1 | * | 8/2024 | Allred | .................. C12Q 1/6853 |

FOREIGN PATENT DOCUMENTS

| | | |
|---|---|---|
| CN | 109988822 A | 7/2019 |
| EP | 3650559 A1 | 5/2020 |
| WO | 2022256143 A1 | 12/2022 |

OTHER PUBLICATIONS

De Silva, Pavani Yashodha, and Gamage Upeksha Ganegoda. "New trends of digital data storage in DNA." BioMed research international 2016.1 (2016): 8072463. (Year: 2016).*

Cohen, et al., "Construction of Biologically Functional Bacterial Plasmids In Vitro", In Proceedings of the National Academy of Sciences, vol. 70, Issue 11, Nov. 1, 1973, pp. 3240-3244.

Grass, et al., "Covalently Functionalized Cobalt Nanoparticles as a Platform for Magnetic Separations in Organic Synthesis", In Angewandte Chemie International Edition, vol. 46, Issue 26, Jun. 25, 2007, pp. 4909-4912.

Holz, et al., "Specificity and Efficiency of the Uracil DNA Glycosylase-Mediated Strand Cleavage Surveyed on Large Sequence Libraries", In Journal of Scientific Reports, vol. 9, Issue 1, Nov. 28, 2019, pp. 1-12.

Jamalzadeh, et al., "High Accuracy Multi-input DNA Logic Gate Using the Spatially Localized DNA Structures", In Proceedings of the 25th International Computer Conference, Computer Society of Iran, Jan. 1, 2020, 8 Pages.

Meiser, et al., "Synthetic DNA Applications in Information Technology", In Journal of Nature Communications, vol. 13, Issue 1, Jan. 17, 2022, pp. 1-13.

Miller, et al., "Basic Concepts of Microarrays and Potential Applications in Clinical Microbiology", In Journal of Clinical Microbiology Reviews, vol. 22, Issue 4, Oct. 2009, pp. 611-633.

"International Search Report and Written Opinion Issued in PCT Application No. PCT/US23/010534", Mailed Date: May 9, 2023, 14 Pages.

(Continued)

*Primary Examiner* — Robert J Yamasaki
(74) *Attorney, Agent, or Firm* — Benjamin Keim; Newport IP, LLC

(57) ABSTRACT

Sequential assembly of oligonucleotide hairpins is used to create oligonucleotides with specific sequences. Each oligonucleotide hairpin includes a payload region containing one or more nucleotides that are added to the end of an anchor strand. Overhang regions on the oligonucleotide hairpins hybridize to anchor strands attached to a substrate. The hybridized oligonucleotide hairpins are covalently attached to the anchor strands by the activity of ligase. The oligonucleotide hairpins include an enzyme cleavage region which, when cleaved, separates the payload region from the remainder of the oligonucleotide hairpin. The oligonucleotide hairpin is separated from the anchor strand by denaturation and washed away. This process is repeated with additional oligonucleotide hairpins to add additional nucleotides to the ends of the anchor strands. A microelectrode array may be used to control the location of hybridization and create multiple oligonucleotides in parallel. Fully assembled oligonucleotides can be separated from the substrate and stored.

20 Claims, 7 Drawing Sheets

(56) References Cited

OTHER PUBLICATIONS

"International Search Report and Written Opinion Issued in PCT Application No. PCT/US23/010535", Mailed Date: May 9, 2023, 14 Pages.

Takahashi, et al., "Demonstration of End-to-End Automation of DNA Data Storage", In Journal of Scientific Reports, vol. 9, Issue 1, Mar. 21, 2019, 5 Pages.

Willsey, et al., "Puddle: A Dynamic, Error-Correcting, Full-Stack Microfluidics Platform", In Proceedings of the Twenty-Fourth International Conference on Architectural Support for Programming Languages and Operating Systems, Apr. 13, 2019, pp. 183-197.

Zhang, et al., "Control of DNA Strand Displacement Kinetics Using Toehold Exchange", In Journal of the American Chemical Society, vol. 131, Issue 47, Dec. 2, 2009, pp. 17303-17314.

Kishi, et al., "Programmable Autonomous Synthesis of Single-Stranded DNA", In Journal of Nature Chemistry, vol. 10, No. 2, Nov. 6, 2017, 10 Pages.

Non-Final Office Action mailed on Dec. 12, 2025, in U.S. Appl. No. 17/670,350, 10 pages.

Wei et al., "Production of dumbbell probe through hairpin cleavage-ligation and increasing RCA sensitivity and specificity by circle to circle amplification", Scientific Reports, Jul. 7, 2016, 13 pages.

* cited by examiner

Figure 2A:
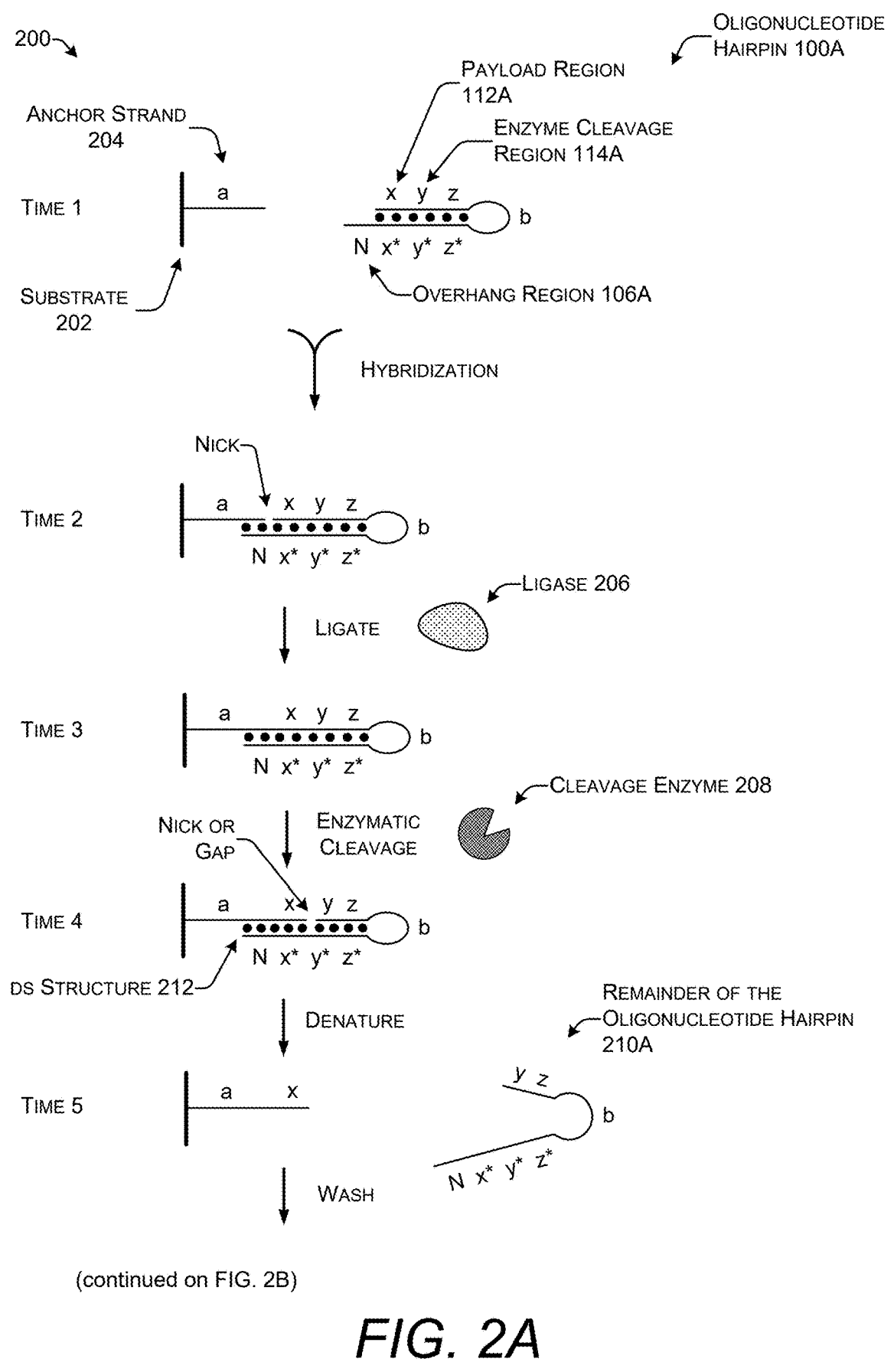

200

OLIGONUCLEOTIDE
HAIRPIN 100A

PAYLOAD REGION
112A

ANCHOR STRAND
204

ENZYME CLEAVAGE
REGION 114A

TIME 1 a x   y   z b

N   x*   y*   z*

SUBSTRATE
202

OVERHANG REGION 106A

HYBRIDIZATION

NICK

TIME 2 a x   y   z b

N   x*   y*   z*

LIGASE 206

LIGATE

TIME 3 a x   y   z b

N   x*   y*   z*

CLEAVAGE ENZYME 208

NICK OR
GAP

ENZYMATIC
CLEAVAGE

TIME 4 a x   y   z b

N   x*   y*   z*

DS STRUCTURE 212

DENATURE

REMAINDER OF THE
OLIGONUCLEOTIDE HAIRPIN
210A

TIME 5 a   x y   z b

N   x*   y*   z*

WASH

Figure 3:
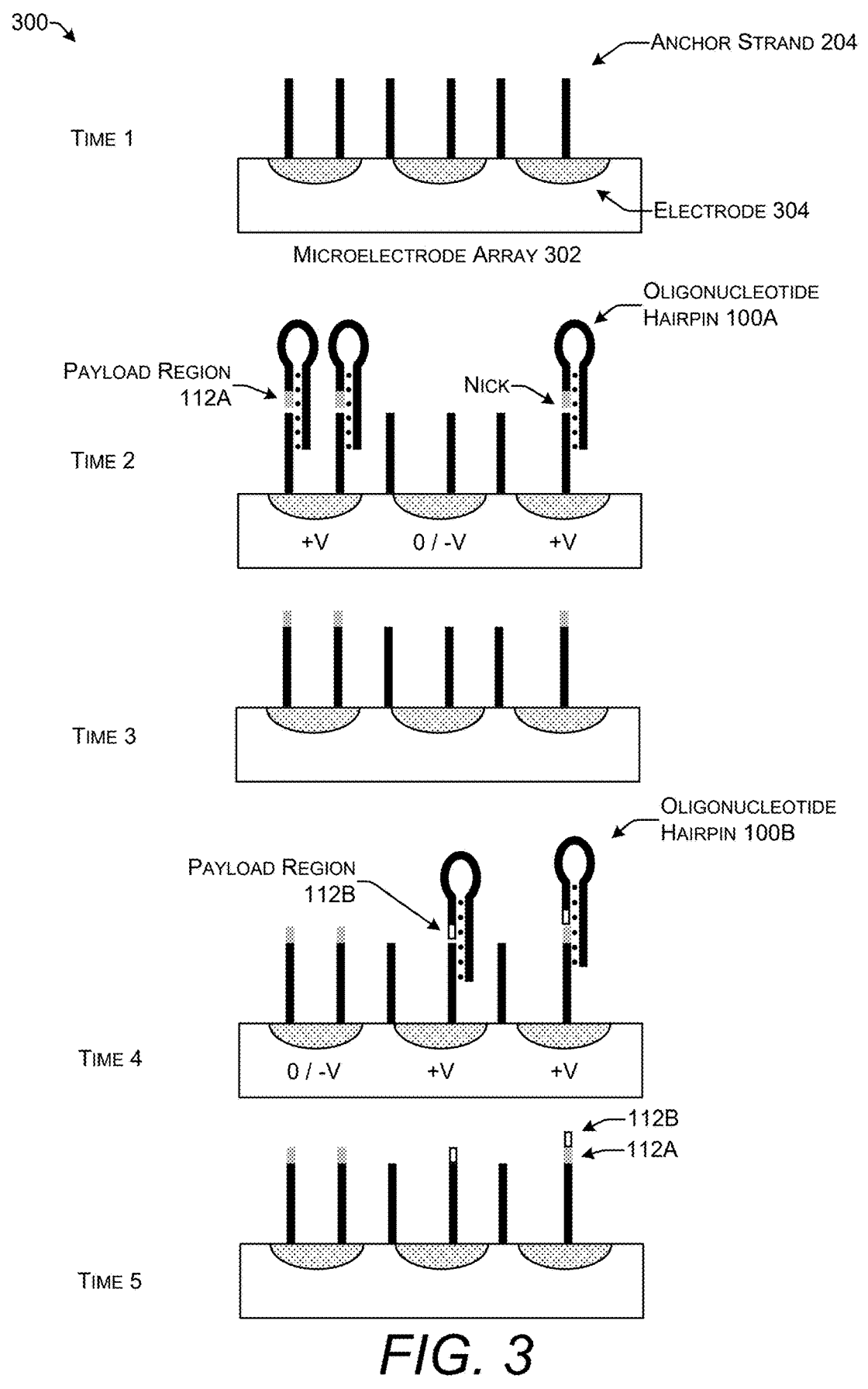

ANCHOR STRAND 204

TIME 1

ELECTRODE 304

MICROELECTRODE ARRAY 302

OLIGONUCLEOTIDE
HAIRPIN 100A

PAYLOAD REGION
112A

NICK

TIME 2

+V    0 / -V    +V

TIME 3

OLIGONUCLEOTIDE
HAIRPIN 100B

PAYLOAD REGION
112B

TIME 4

0 / -V    +V    +V 112B
112A

TIME 5

ENZYMATIC OLIGONUCLEOTIDE ASSEMBLY USING HAIRPINS AND ENZYMATIC CLEAVAGE

BACKGROUND

De novo synthesis of oligonucleotides has many applications including data storage. Synthetic oligonucleotides, such as deoxyribose nucleic acid (DNA), can be used to store digital information with a much higher density and greater longevity than conventional media. Examples of data storage and other information technology applications for synthetic DNA are discussed in Meiser, L. C., Nguyen, B. H., Chen, Y J. et al. Synthetic DNA applications in information technology. *Nat Commun* 13, 352 (2022).

The vast majority of artificially synthesized oligonucleotides are created by chemical synthesis using the phosphoramidite process. This process involves multiple steps and is performed using the organic solvent acetonitrile. However, the phosphoramidite process is complex and creates waste that can be hazardous and expensive to process.

Oligonucleotides may also be synthesized with a template-independent DNA polymerase called terminal deoxynucleotidyl transferase (TdT). Enzymatic synthesis addresses some of the deficiencies of the phosphoramidite process. However, this enzyme can repeatedly add the same nucleotide multiple times creating unintended homopolymers. A variety of techniques have been identified to limit homopolymer creation, but each increases complexity and comes with its own set of draw backs.

Alternative ways of creating oligonucleotides with specific, controllable sequences will be useful for information technology and other applications. The following disclosure is made with respect to these and other considerations.

SUMMARY

This disclosure provides methods, oligonucleotide structures, and devices for assembling oligonucleotides by repeated hybridization of oligonucleotide hairpins to anchor strands. A substrate coated with single-stranded oligonucleotide anchor strands is contacted with an oligonucleotide hairpin. Each oligonucleotide hairpin has a stem region, a loop region, and a single-stranded overhang region that extends from the stem region. Sequences of the oligonucleotide hairpins and the anchor strands are designed so that the overhang regions hybridize to the anchor strands. Ligase is used to form a nucleotide backbone between the hybridized oligonucleotide hairpins and ends of the anchor strands. The portion of the oligonucleotide hairpin that is directly ligated to the anchor strand is a payload region. The payload region includes one or more arbitrary nucleotides. For example, the payload region may contain a single nucleotide with any one of the standard bases adenine (A), guanine (G), cytosine (C), thiamine (T), or uracil (U).

Enzymatic cleavage is then used to cut each oligonucleotide hairpin between the payload region and the rest of the oligonucleotide hairpin. Thus, the payload region remains covalently attached to the anchor strand while the remainder of the oligonucleotide hairpin is held in place by Watson-Crick base pairing. The specific enzyme and type of enzymatic cleavage used depend on the sequence of the oligonucleotide hairpin that is directly adjacent to the payload region. For example, any of uracil DNA Glycosylase (UDG), ribonuclease H, a restriction enzyme, or a nicking enzyme may be used for enzymatic cleavage.

The complex formed by hybridization of the anchor strand and the oligonucleotide hairpin (following cleavage of the payload region) is denatured. This releases the remainder of the oligonucleotide hairpin. Heat or any other suitable technique may be used to denature. The unbound oligonucleotide hairpins are then washed away leaving an anchor strand extended by the addition of the payload region.

This process is repeated with another oligonucleotide hairpin. Each round of addition adds the contents of another payload region to the end of the anchor strand. This creates an oligonucleotide with an arbitrary sequence of nucleotides without the use of phosphoramidite chemistry or template-independent polymerase. The sequence of nucleotides may encode a specific string of arbitrary information such as digital data. Alternatively, the sequence of nucleotides may encode biological information such as a gene or gene fragment. After an oligonucleotide having the intended sequence of nucleotides is created, it may be released from the substrate and stored or used.

Multiple oligonucleotides with different sequences may be created in parallel by using a microelectrode array as the substrate. Selective activation of electrodes in the microelectrode array creates localized electric fields that attract the oligonucleotide hairpins to specific locations on the surface of the substrate. Oligonucleotide hairpins hybridize to the anchor strands in proximity to the activated electrodes. The location of oligonucleotide hybridization may be varied during subsequent rounds of assembly. This results in a high degree of parallelism and synthesis of multiple oligonucleotides with different sequences.

Automated or semi-automated systems may be used to introduce oligonucleotide hairpins, ligase, and cleavage enzymes to the surface of a substrate to create oligonucleotides with specific sequences. Such systems may be computer controlled and selectively bring oligonucleotide hairpins with payload regions containing specific nucleotides into contact with anchor strands on the substrate in an order to create oligonucleotides with specific sequences.

This Summary is provided to introduce a selection of concepts in a simplified form that are further described below in the Detailed Description. This Summary is not intended to identify key features or essential features of the claimed subject matter nor is it intended to be used to limit the scope of the claimed subject matter. The term "techniques," for instance, may refer to system(s) and/or method(s) as permitted by the context described above and throughout the document.

BRIEF DESCRIPTION OF THE DRAWINGS

The Detailed Description is set forth with reference to the accompanying figures. In the figures, the left-most digit(s) of a reference number identifies the figure in which the reference number first appears. The use of the same reference numbers in different figures indicates similar or identical items. The figures are schematic representations and items shown in the figures are not necessarily to scale.

FIGS. 2A and 2B are a time series illustrating the creation of oligonucleotides with specific sequences by sequential hybridization, ligation, and enzymatic cleavage of oligonucleotide hairpins.

FIG. 3 is a time series illustrating the use of a microelectrode array to control the location of oligonucleotide hairpin hybridization.

DETAILED DESCRIPTION

Figure 1:
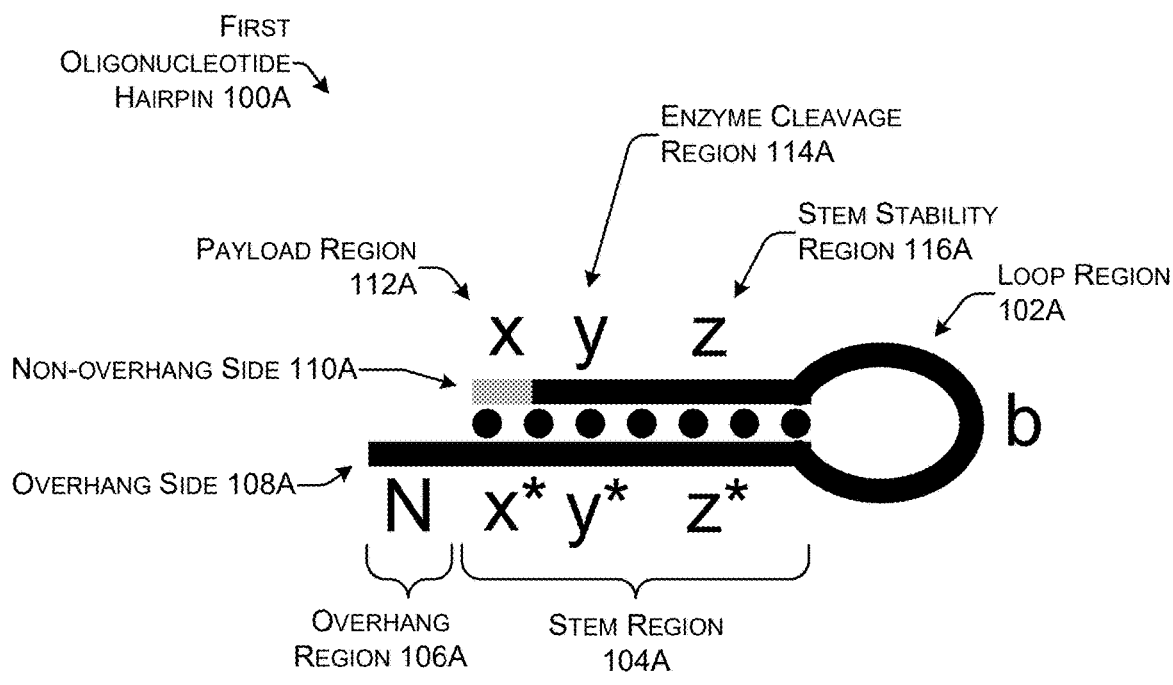
FIG. 1 is a diagram illustrating example structures of two oligonucleotide hairpins.
Figure 1:
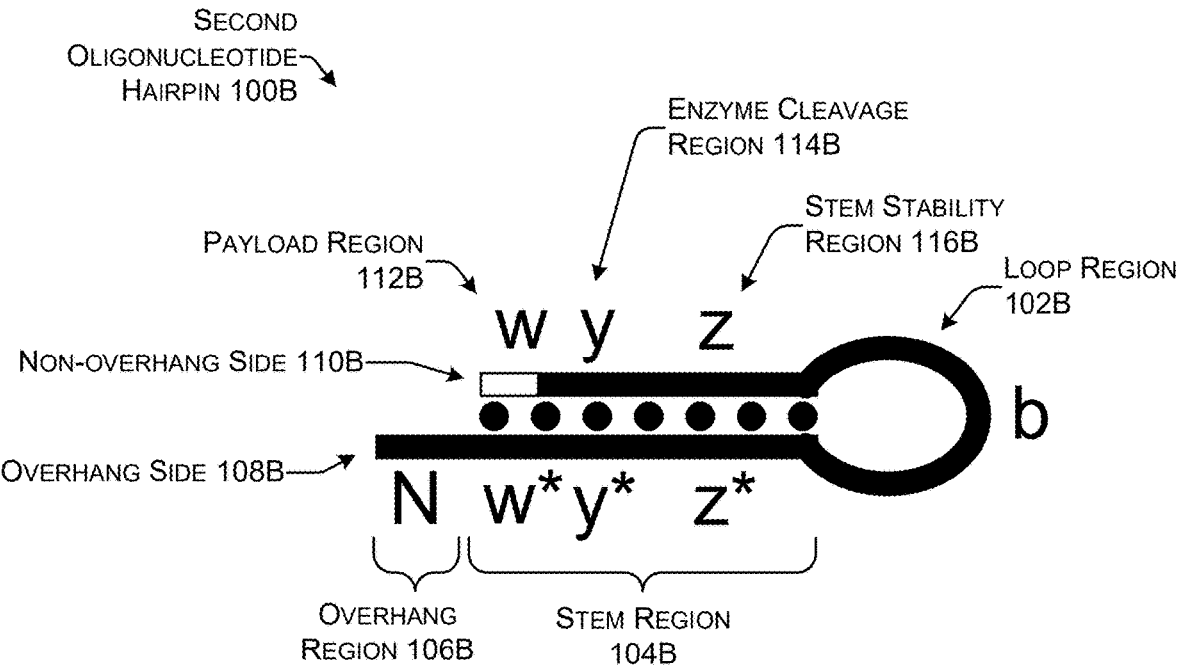

This disclosure provides techniques that use hybridization between overhanging ends of oligonucleotide hairpins and anchor strands to assemble oligonucleotides without using standard chemical synthesis techniques or template-independent polymerase. The disclosed technique for assembling oligonucleotides can be implemented by using only pre-synthesized oligonucleotides hairpins, the enzyme ligase, and a cleavage enzyme. The oligonucleotide hairpins are joined to and append nucleotides to the end of anchor strands attached to a solid substrate. Thus, this disclosure provides a novel technique for solid-state oligonucleotide synthesis. A single oligonucleotide hairpin may append one or more nucleotides to the end of an anchor strand.

In one implementation, the sequence of the added nucleotides encodes arbitrary information. For example, the arbitrary information may be binary digits (e.g., 0 and 1). Oligonucleotides that encode binary digits may be used to encode digital information. Encoding schemes for representing binary digits with nucleotide sequences are known to those of ordinary skill in the art. Any other type of arbitrary information such as trits or ASCII characters may also be encoded.

These techniques are readily adapted for automated or semiautomated systems such as microfluidic or laboratory robotics systems. The use of a microelectrode array allows for the massively parallel creation of a large number of oligonucleotides with different sequences. This technique can be used for the efficient encoding of a large amount of arbitrary information. The technique may also create oligonucleotides with any arbitrary sequence such as a sequence with biological meaning like a gene or gene fragment. One application for the techniques of this disclosure is a DNA data storage center. In a DNA data storage center, a large amount of digital information is encoded in oligonucleotides such as DNA. A DNA data storage center may continually write digital information through the synthesis of oligonucleotides. If done with the conventional phosphoramidite technique, such a large amount of de novo synthesis would generate significant amounts of hazardous organic waste.

Oligonucleotides, also referred to as polynucleotides, include both DNA, ribonucleic acid (RNA), and hybrids containing mixtures of DNA and RNA. DNA includes nucleotides with one of the four natural bases cytosine (C), guanine (G), adenine (A), or thymine (T) as well as unnatural bases, noncanonical bases, and modified bases. RNA includes nucleotides with one of the four natural bases cytosine, guanine, adenine, or uracil (U) as well as unnatural bases, noncanonical bases, and modified bases.

Detail of procedures and techniques not explicitly described or other processes disclosed in this application are understood to be performed using conventional molecular biology techniques and knowledge readily available to one of ordinary skill in the art. Specific procedures and techniques may be found in reference manuals such as, for example, Michael R. Green & Joseph Sambrook, *Molecular Cloning: A Laboratory Manual*, Cold Spring Harbor Laboratory Press, 4$^{th}$ ed. (2012).

FIG. 1 illustrates the structure of the oligonucleotide hairpins 100 described in this disclosure. Oligonucleotide hairpins 100 may be created by conventional phosphoramidite synthesis, enzymatic synthesis, or any other technique such as cloning in bacteria. An oligonucleotide hairpin 100 includes a single-stranded loop region 102, a double-stranded stem region 104, and a single-stranded overhang region 106. To form a loop structure, the loop region 102 is typically at least 3 nucleotides. The loop region 102 may be longer than 3 nucleotides. As discussed in more detail below, the overhang region 106 hybridizes to the end of an anchor strand. To provide sufficiently strong hybridization, the overhang region 106 may be at least 3 nucleotides or at least 4 nucleotides. The overhang region 106 may also be longer than 4 nucleotides.

The stem region 104 includes two sides that hybridize to each other. The side of the stem region 104 that includes the overhang region 106 is referred to as the overhang side 108. The side of the stem region 104 that does not have the overhang region 108 is referred to as the non-overhang side 110. The notation of "n*" indicates a sequence that hybridizes to or is complementary to "n" where "n" represents a single-stranded oligonucleotide sequence. Thus, "a*" hybridizes to sequence "a", "b*" hybridizes to sequence "b", and so forth. Sequences with less than full complementarity may hybridize to each other. Hybridization between two single-stranded oligonucleotides is represented as a series of black dots.

The stem region 104 includes a payload region 112 at the end of the non-overhang side 110. The payload region 112 includes at least one nucleotide. The payload region 112 may be a nucleotide with any of the canonical bases: A, G, C. T, or U. In one implementation, there are four different species oligonucleotide hairpins 100 each having a single nucleotide in the payload region 112 containing a different one of the four canonical bases found in either DNA or RNA. In one implementation, the payload region 112 includes two nucleotides. In this implementation, there are 16 different species of oligonucleotide hairpins 100 each containing in the payload region 112 a different combination of two nucleotides (e.g., in DNA the combinations are AA, AG, AC, AT, GA, GG, GC, GT, CA, CG, CC, CT, TA, TG, TC, and TT). Longer payload regions are also possible and would use a correspondingly greater number of different species of oligonucleotide hairpins 100.

The payload region 112 may also contain one or more nucleotides that encode arbitrary information. As an example of a simple encoding scheme, a single nucleotide may encode a bit value such as A=0 and G=1. The sequence of a payload region 112 may also use multiple nucleotides to encode a bit value such as CTA=1 and ACG=0. The payload region 112 may encode trits, letters of the English alphabet, or any other type of arbitrary information. The number of different variations of the payload region 112 will depend on the number of different pieces of arbitrary information that are encoded (e.g., two different payload regions for encoding bits, 26 different payload regions for encoding letters of the English alphabet, etc.). In an implementation, the payload region 112 may use 2-5 nucleotides to encode arbitrary information. However, the payload region 112 may also be longer than 5 nucleotides.

The stem region 104 additionally includes an enzyme cleavage region 114 that can be cleaved by a cleavage enzyme which separates the payload region 112 from the remainder of the oligonucleotide hairpin. The enzyme cleavage region 114 may, in some implementations, contain only a single nucleotide that can be recognized by a cleavage enzyme. For example, the single nucleotide may be as a uracil DNA or an RNA nucleotide in an oligonucleotide that otherwise contains only DNA nucleotides.

The enzyme cleavage region 114 may, alternatively, contain multiple nucleotides that are a cut site for a restriction enzyme or a nicking enzyme. The enzyme cleavage region 114 is directly adjacent to the payload region 112. That is, there are no nucleotides between the payload region 112 and the enzyme cleavage region 114. With this structure, if the oligonucleotide hairpin 100 is cut at the enzyme cleavage region 114, the nucleotides of the payload region 112 are separated from the remainder of the oligonucleotide hairpin and free from any additional nucleotides that are not part of the payload region 112.

The stem region 104 may optionally include a stem stability region 116. The stem stability region 116 increases the length of the stem region 104 and provides greater stability to the hairpin structure. In an implementation, the entire stem region 104 is at least 6 nucleotides. Thus, for example, if the payload region 112 and the enzyme cleavage region 114 each include only a single nucleotide then the stem stability region 116 will contain at least 4 nucleotides. However, if for example, the payload region 112 contains 5 nucleotides and the enzyme cleavage region 114 contains 4 nucleotides, then the total length of the stem region 104 is 9 nucleotides without a stem stability region 116. Thus, the stem stability region 116 may have a length that, when combined with the length of the payload region 112 and the enzyme cleavage region 114, results in a length of the stem region 104 being at least 6 nucleotides.

Techniques for designing stable hairpin structures are well known to those of ordinary skill in the art. Oligonucleotide hairpins may be designed using software created for that purpose such as, but not limited to, NUPACK available from nupack.org. For a discussion of the NUPACK software see J. N. Zadeh, C. D. Steenberg, J. S. Bois, B. R. Wolfe, M. B. Pierce, A. R. Khan, R. M. Dirks, N. A. Pierce. NUPACK: analysis and design of nucleic acid systems. *J Comput Chem*, 32:170-173, 2011.

The total length of an oligonucleotide hairpin 100 is typically at least 18 nucleotides. For example, an oligonucleotide hairpin 100 with an overhang region 106 containing 3 nucleotides, a stem region 104 that is 6 nucleotides on each side, and a loop region 102 that is 3 nucleotides will have a total length of 18 nucleotides. As an additional example, if the overhang region 106 is 4 nucleotides, the loop region 102 contains 5 nucleotides, and each side of the stem region 104 contains 15 nucleotides (e.g., a payload region 112 of 5 nucleotides, an enzyme cleavage region 114 of 4 nucleotides, and a stem stability region 116 of 6 nucleotides), then the total length of the oligonucleotide hairpin 100 will be 39 nucleotides.

Any of the overhang region 106, the stem region 104, and the loop region 102 may be longer than the example lengths provided above. Thus, there is no absolute upper limit on the length of an oligonucleotide hairpin 100. However, there is additional cost and effort associated with generating longer oligonucleotide sequences, so the shortest functional sequences may generally be preferred. Accordingly, in some implementations, the total length of an oligonucleotide hairpin 100 may be about 18-40 nucleotides.

FIG. 1 illustrates a collection of oligonucleotide hairpins: a first oligonucleotide hairpin 100A and a second oligonucleotide hairpin 100B. However, the techniques of this disclosure may be implemented with a greater number of oligonucleotide hairpin species. The first oligonucleotide hairpin 100A includes a first loop region 102A, a first stem region 104A, and a first overhang region 106A. The second oligonucleotide hairpin 100B includes a second loop region 102B, a second stem region 104B, and a second overhang region 106B. The stem regions 104A. 104B each include a respective payload region 112A, 112B, enzyme cleavage region 114A. 114B, and optional stem stability region 116A. 116B.

These two oligonucleotide hairpins 100A. 100B differ in the nucleotides encoded in their respective payload regions 112A, 112B. For example, the first payload region 112A and the second payload region 112B may both be the same length or they may be different lengths. Thus, the first payload region 112A and the second payload region 112B may each independently include 1, 2, 1-5, or 2-5 nucleotides. In an implementation, the first payload region 112A may encode first arbitrary information (e.g., the binary digit 0) and the second payload region 112B may encode second arbitrary information (e.g., the binary digit 1).

The nucleotide sequences of the first oligonucleotide hairpin 100A and the second oligonucleotide hairpin 100B may be identical other than the sequences of the respective payload regions 112A. 112B and the portion of the stem regions 104A. 104B that hybridize to the respective payload regions 112A, 112B, Thus, the loop regions 102A. 102B, the overhang regions 106A. 106B, the enzyme cleavage regions 114A. 114B, and the stem stability regions 116A, 116B may include identical sequences of nucleotides. In some implementations, the overhang regions 106A, 106B may also be different from each other with all other portions of the oligonucleotide hairpins 100A, 100B the same.

As mentioned above, synthesis of the oligonucleotide hairpins 100 may be performed by any technique suitable for generating oligonucleotides with specific sequences such as conventional phosphoramidite synthesis. The techniques of this disclosure may be used to assemble oligonucleotides with any arbitrary nucleotide sequence from only oligonucleotide hairpins 100, the enzyme ligase, and a cleavage enzyme. Thus, this process in itself does not use conventional phosphoramidite synthesis or require hazardous chemicals such as acetonitrile. However, if the oligonucleotide hairpins 100A. 100B are themselves are created by phosphoramidite synthesis there is no net reduction in the use of hazardous chemicals. Rather, acetonitrile use and associated waste disposal are merely shifted from the site of oligonucleotide assembly to the site of oligonucleotide hairpin 100 synthesis.

However, there are techniques to manufacture many copies of an oligonucleotide sequence without phosphoramidite synthesis by cloning the sequence in bacteria. Techniques that use bacterial cloning to make multiple copies of a gene are well known to those of ordinary skill in the art. See Cohen S N, Chang A C, Boyer H W, Helling R B. Construction of biologically functional bacterial plasmids in vitro. *Proc Natl Acad Sci USA*. 1973 November; 70(11). The oligonucleotide sequences that form the oligonucleotide hairpins 100 may be added to and manufactured in bacteria in the same manner as the DNA of a gene.

For example, oligonucleotide sequences corresponding to each of multiple different oligonucleotide hairpin species may be inserted into plasmids and grown in *E. coli*. The specific oligonucleotide sequences may then be cut from the plasmids and purified using conventional techniques. One technique for producing single-stranded DNA that forms hairpins in *E. coli* is described in Ducani et al., Enzymatic production of 'monoclonal stoichiometric' single-stranded DNA oligonucleotides. *Nature Methods*, 10:7, 2013. Accordingly, in some implementations, the oligonucleotide hairpins 100 are created by cloning in bacteria. The purified products of the bacteria cloning may then be stored in separate containers and used as needed for oligonucleotide assembly according to the techniques of this disclosure.

Figure 2B:
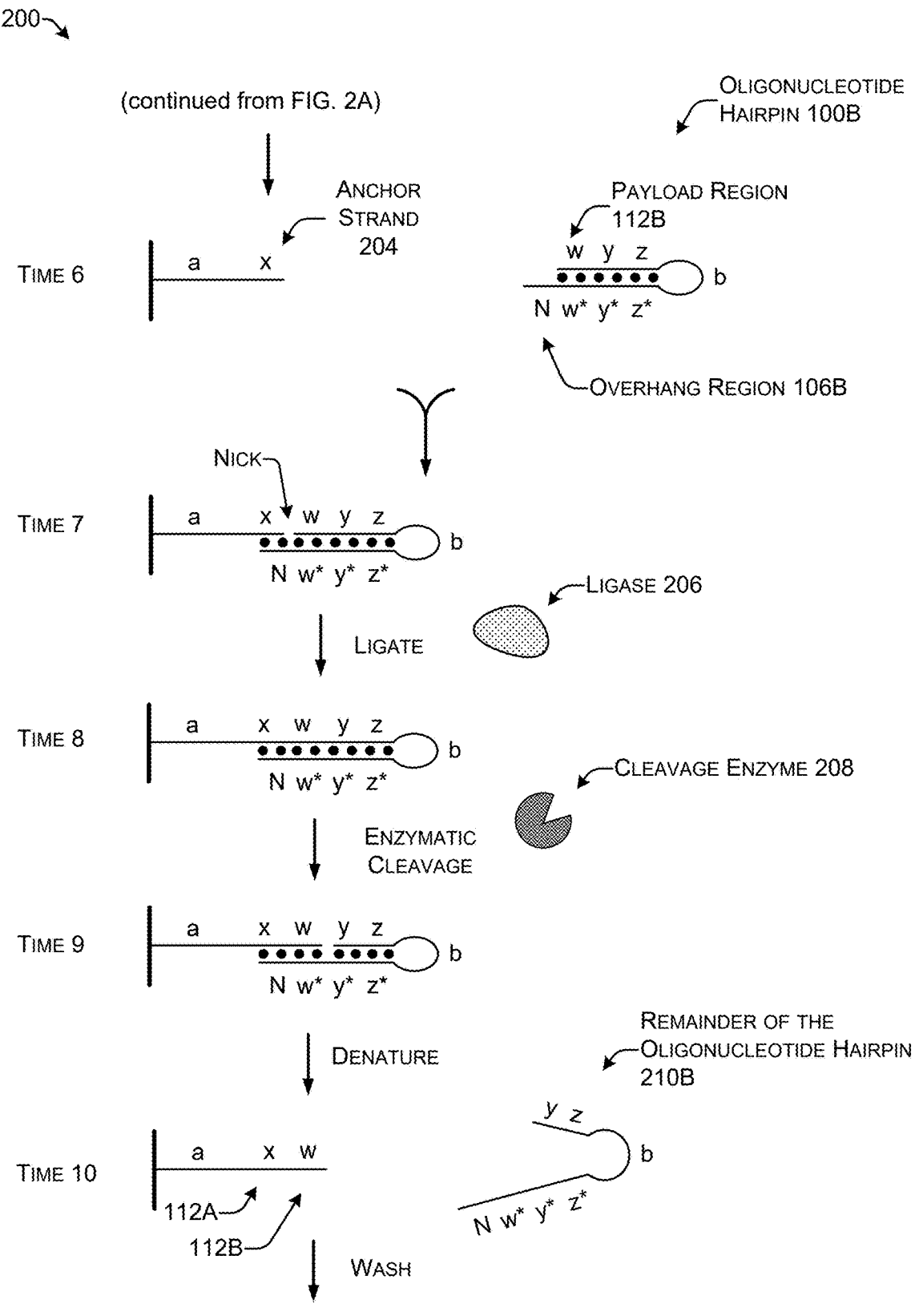

FIGS. 2A and 2B show a time series 200 that illustrates the creation of oligonucleotides with specific sequences of nucleotides by sequential hybridization, ligation, and enzymatic cleavage of oligonucleotide hairpins 100. Assembly of the oligonucleotide begins at Time 1 with a substrate 202 that is coated with anchor strands 204. The substrate 202 may be any type of substrate 202 suitable for solid-phase oligonucleotide synthesis. Persons of ordinary skill in the art can readily select an appropriate substrate. The substrate 202 may be formed from a material such as glass, silicon, or plastic. In an implementation, the substrate 202 is a flat or substantially flat surface such as a silicon chip or glass slide. In an implementation, the substrate 202 is a bead or microsphere. The substrate 202 may also be implemented as magnetic nanoparticles one example of which are "Turbo-Beads®" available from TurboBeads LLC (Zürich, Switzerland). TurboBeads are described in Grass et al., *Covalently Functionalized Cobalt Nanoparticles as a Platform for Magnetic Separations in Organic Synthesis,* 46 Angew. Chem. Int. Ed. 4909 (2007).

The anchor strands 204 on the substrate 202 are single-stranded oligonucleotides. The anchor strands 204 may be synthesized by conventional phosphoramidite synthesis, enzymatic synthesis, or any other technique. Each anchor strand 204 may be about 9-11 nucleotides or 5-15 nucleotides. However, the anchor strands 204 may be longer or shorter. Although only a single anchor strand 204 is illustrated in FIG. 2, the substrate 202 may be coated with thousands or millions of individual anchor strands 204. In an implementation, all anchor strands 204 have the same sequence of nucleotides. There may also be other implementations in which there are multiple different anchor strands 204 with different sequences over at least part of their lengths.

The anchor strands 204 may be attached to the substrate 202 by any known technique for coating a solid substrate with oligonucleotides. Multiple techniques are known to those of ordinary skill in the art including techniques used to generate DNA microarrays such as spotting or printing with an inkjet-like printer, in situ synthetization, and bead arrays. For discussion of different microarray platforms that may be used to generate a solid substrate coated with oligonucleotides see Miller M B, Tang Y W. *Basic concepts of microarrays and potential applications in clinical microbiology.* Clin Microbiol Rev. 2009 October; 22(4): 611-33.

The substrate 202 may, in some implementations, be functionalized to provide for attachment of the anchor strands 204. Examples include silane functionalization which covers a surface with organofunctional alkoxysilane molecules or agarose functionalization which covers a surface with a polysaccharide matrix. Linkers may be used to attach the anchor strands 204 to the surface of the substrate 202. Examples of linkers that may be used are provided in U.S. Pat. Pub. No. 2020/0199662 filed on Dec. 21, 2018, with the title "Selectively Controllable Cleavable Linkers." Non-covalent attachment such as streptavidin-biotin interactions may also be used to attach the anchor strands 204 to the substrate 202. These and other techniques for attaching single-stranded oligonucleotides to a solid substrate are well known to those of ordinary skill in the art.

In this example time series 200, the anchor strand 204 is contacted with a first oligonucleotide hairpin 100A at Time 1. As described above, the first oligonucleotide hairpin 100A includes a first overhang region 106A, first payload region 112A, and a first enzyme cleavage region 114A. The anchor strand 204 may be contacted with the first oligonucleotide hairpin 100A by bringing a solution containing many copies of the first oligonucleotide hairpin 100A into contact with the surface of the substrate 202.

Time 2 illustrates hybridization between the first overhang region 106A of the first oligonucleotide hairpin 100A and the end of the anchor strand 204. The number of nucleotides on the end of the anchor strand 204 that are equal to the length of the first overhang region 106A hybridize to the first oligonucleotide hairpin 100A. For example, if the first overhang region 106A contains 4 nucleotides, it will hybridize to the final 4 nucleotides on the end of anchor strand 204. Thus, the sequence of the first overhang region 106A represented by "N" hybridizes to the corresponding number of nucleotides on the end of the anchor strand 204. In some implementations, the sequence of the first overhang region 106A is specifically designed to be fully complementary to the end portion of the anchor strand 204. For example, if the final 4 nucleotides of the anchor strand 204 are GACG then the sequence of the first overhang region 106A may be CTGC. However, sequences that are less than fully complementary but still hybridize can also be used.

Hybridization between the first oligonucleotide hairpin 100A and the anchor strand 204 positions the nucleotide(s) of the payload region 112A adjacent to the nucleotide on the end of the anchor strand 204. This is illustrated in FIG. 2 at Time 2 by "x" being positioned adjacent to "a." Preferentially, the payload region 112A is directly adjacent to the end of the anchor strand 204 such that there is no space for an additional nucleotide in between. This results in a nick in the backbone of the double-stranded oligonucleotide formed from a/N and x/x*. In some implementations, there may be a one or two nucleotide gap between the payload region 112A and the end of the anchor strand 204. However, ligation efficiency will decrease if the ends are not directly adjacent.

Time 3 shows a connection formed between the first oligonucleotide hairpin 100A and the anchor strand 204 following contact with ligase 206. Nicks in an oligonucleotide backbone may be closed by ligation. Techniques for performing ligation and closing of nicks in DNA and RNA are well-known to those of ordinary skill in the art. For example, techniques used to join DNA fragments in Golden Gate Assembly may be readily adapted for use in ligating the first oligonucleotide hairpin 100A to the anchor strand 204. In some implementations, the ligase 206 may be added at the same time as the first oligonucleotide hairpin 100A. Thus, the time series 200 may proceed from Time 1 directly to Time 3 without a separate step for addition of the ligase 206.

Ligases for both DNA and RNA are known. DNA ligase is a specific enzyme that joins DNA strands together by catalyzing the formation of a phosphodiester bond. One specific type of DNA ligase that is frequently used in molecular biology is T4 DNA Ligase isolated from bacteriophage T4. T4 DNA ligase is most active at 37° C. RNA ligase (ATP) is an analogous enzyme that catalyzes the formation of phosphodiester bonds between ribonucleotides. One commercially available RNA ligase suitable for closing nicks is T4 RNA ligase 2. T4 RNA ligase 2 is also most active at 37° C. DNA and RNA ligases including appropriate ligase buffers are available from multiple commercial sources. For example, a ligase buffer may contain 50 mM Tris-HCl, 10 mM MgCl$_2$, 1 mM ATP, 10 mM DTT, with pH 7.5 at 25° C.

For optimal ligation efficiency with hairpin structures, the optimal temperature for the enzyme is balanced with the melting temperature $T_m$ of the structure being ligated because hybridization may be disrupted by high temperatures. If hybridization between the oligonucleotide hairpin 100 and anchor strand 204 would be disrupted at optimal temperatures for the ligase 206, a lower temperature may be used. Persons of ordinary skill in the art will understand how to calculate $T_m$ for a given double-stranded structure and adjust the ligation temperature appropriately.

Time 4 shows enzymatic cleavage of the first enzyme cleavage region 114A. The enzymatic cleavage removes at least the phosphodiester backbone between a nucleotide of the first payload region 112A and the adjacent nucleotide of the first enzyme cleavage region 114A. Enzymatic cleavage may also remove one or more nucleotides from the enzyme cleavage region 114A. Contacting the oligonucleotide with a cleavage enzyme 208 creates a nick or gap between the first payload region 112A and the first enzyme cleavage region 114A (i.e., between "x" and "y"). This breaks the covalent connection between nucleotides of the first payload region 112A the remainder of the first oligonucleotide hairpin 210A.

Persons of ordinary skill in the art are familiar with multiple techniques for enzymatic cleavage of double-stranded oligonucleotide structures. Any technique that uses enzymatic digestion of oligonucleotides to create a nick or gap between the payload region 112 and the enzyme cleavage region 114 may be used. This includes techniques known to those of ordinary skill in the art in addition to those explicitly listed here as well as any later developed techniques.

One technique to create a gap at a specific location in an oligonucleotide uses a combination of Uracil DNA glycosylase (UDG) and the DNA glycosylase-lyase Endonuclease VIII to remove a uracil base. Oligonucleotide cleavage mediated by UDG consists of two separate steps: excision of the uracil base followed by cleavage of the resulting abasic site. Thus, in one implementation, the enzyme cleavage region 114 is a single uracil DNA and the cleavage enzyme 208 comprises uracil DNA Glycosylase (UDG) and an endonuclease.

The generation of a single-nucleotide gap in double-stranded DNA using this technique is described in Holz, K., Pavlic, A., Lietard, J. et al. Specificity and Efficiency of the Uracil DNA Glycosylase-Mediated Strand Cleavage Surveyed on Large Sequence Libraries. *Sci Rep* 9, 17822 (2019). A commercial product for performing this digestion, the USER® (Uracil-Specific Excision Reagent) enzyme product is available from New England Biolabs (USA). Digestion may be performed using the protocol provided by the commercial supplier of the enzyme. The digestion is performed in a suitable buffer which may be provided by the supplier of the enzyme. For example, the buffer provided with the USER® enzyme comprises 50 mM Potassium Acetate, 20 mM Tris-acetate. 10 mM Magnesium Acetate, and 100 µg/ml Recombinant Albumin (pH 7.9@25° C.).

Another technique for creating a gap in a double-stranded oligonucleotide uses the RNA cutting enzyme Ribonuclease H (abbreviated RNase H). RNase H is a non-sequence-specific endonuclease that specifically hydrolyzes the phosphodiester bonds of RNA that is hybridized to DNA. This enzyme does not digest single or double-stranded DNA. Thus, in one implementation, the anchor strand 204 and the oligonucleotide hairpin 100 are DNA but the enzyme cleavage region 114 is one or more RNA nucleotides and the cleavage enzyme 208 comprises RNase H. RNase H is available from multiple commercial suppliers including New England BioLabs (USA). Digestion may be performed using the protocol provided by a commercial supplier of the enzyme. The digestion is performed in a suitable buffer which may be provided by the supplier of the enzyme. For example, the buffer used for RNase H may comprise 50 mM Tris-HCl, 75 mM KCl, 3 mM $MgCl_2$, and 10 mM DTT (pH 8.3@; 25° C.).

Nicking enzymes may be used to create a nick between the payload region 112A and the remainder of the oligonucleotide hairpin 210. Nicking enzymes hydrolyze only one strand of a double-stranded oligonucleotide, to produce molecules that are "nicked," rather than cleaved. Thus, digestion of the oligonucleotide structure shown at Time 3 with a nicking enzyme can create a nick as shown at Time 4. Multiple different types of nicking enzymes are known. There are three naturally occurring nicking endonucleases: Nt. BstNBI, Nb.BtsI, and Nb.BsrDI. These are the large subunits of heterodimeric restriction enzymes. As such, the catalytic site present in the small subunit that catalyzes the cleavage of the other strand is entirely missing. There are also multiple engineered nicking enzymes. Nicking enzymes, both natural and engineered, are available from commercial suppliers such as New England BioLabs (USA).

Techniques for performing digestions with nicking enzymes are generally the same as techniques for using restriction endonucleases are well known to those of ordinary skill in the art. Digestion may be performed using the protocol supplied by a commercial supplier of the enzyme. Nicking enzyme digests are performed in a suitable buffer which varies depending on the requirements of the specific enzyme. Such buffers are known to those of ordinary skill in the art and may be provided together with the enzymes from a commercial supplier.

If a nicking enzyme is used as the cleavage enzyme 208, then the enzyme cleavage region 114 is designed to include the recognition sequence for the enzyme with the cut site located between the payload region 112 and the enzyme cleavage region 114. A recognition sequence is the oligonucleotide sequence to which the enzyme binds. The cut site is the site of the oligonucleotide sequence where it is cleaved by the enzyme. Thus, the enzyme cleavage region 114 will include the recognition sequence as well as any other nucleotides necessary to position the cut site directly adjacent to the payload region 112. Accordingly, in some implementations, the enzyme cleavage region 114 comprises a recognition site and a cut site and the cleavage enzyme 208 comprises a nicking enzyme that creates a nick at the cut site.

Restriction enzymes may also be used to separate the payload region 112 from the remainder of the oligonucleotide hairpin 210. Restriction enzymes differ from nicking enzymes in that they cut both strands of a double-stranded oligonucleotide. Thus, digestion with a restriction enzyme will cut the oligonucleotide hairpin 100 between the payload region 112 and the enzyme cleavage region 114 as well as cut somewhere on the overhang side 108 of the stem region 104 or potentially within the overhang region 106. This will result in a nick somewhere on the lower strand (i.e., the overhang side 108) of the oligonucleotide hairpin 100 shown in Time 4 (not shown).

Restriction enzymes for use in the techniques of this disclosure are selected so that the cut site is positioned a constant distance outside of the recognition sequence. Thus, the enzyme cleavage region 114 can be designed so that digestion with restriction enzyme cuts between the nucleotides of the payload region 112 and the nucleotides of the enzyme cleavage region 114. Persons of ordinary skill in the art will be able to readily select an appropriate restriction enzyme based on known the relationship between cut sites and recognition sequences. Suitable types of restriction enzymes include, for example, Type IIS restriction enzymes that cleave outside of the recognition sequence and to one side and Type IIP restriction enzymes that have cut sites positioned to one side of, and several bases away from, the recognition sequence. Accordingly, in some implementations, the enzyme cleavage region 114 comprises a recognition site and a cut site and the cleavage enzyme 208 comprises a restriction enzyme that cleaves at the cut site as well as on the other strand of the hairpin.

Hundreds of different restriction enzymes are available from commercial suppliers such as New England BioLabs (USA). Techniques for performing restriction enzyme digests are well known to those of ordinary skill in the art. Digestion may be performed using the protocol provided by a commercial supplier of the enzyme. Restriction enzyme digests are performed in a suitable buffer which varies depending on the requirements of the specific enzyme. Such buffers are well known to those of ordinary skill in the art and may be provided together with the enzymes from a commercial supplier.

Time 5 shows separation of the remainder of the first oligonucleotide hairpin 210A from the anchor strand 204 following denaturation. Contact and digestion with the cleavage enzyme 208 break the covalent bond between the remainder of the first oligonucleotide hairpin 210A and the anchor strand 204. Denaturation breaks the hydrogen bonds holding the oligonucleotides together through hybridization. The double-stranded structure 212 formed from hybridization of the first oligonucleotide hairpin 100A and the anchor strand 204 (e.g., "a/x" hybridized to "N/x*") is denatured. The hairpin structure may be denatured as well. Thus, at Time 5 the remainder of the first oligonucleotide hairpin 210A separates from the anchor strand 204. At this point the anchor strand 204 is now extended by the addition of the first payload region 112A as shown by the "x" at the end of the anchor strand 204.

Denaturation of the double-stranded structure that exists following digestion with the cleavage enzyme may be performed using any technique suitable for denaturation of double-stranded oligonucleotides. Multiple techniques for denaturing oligonucleotides are known to those of ordinary skill in the art. Techniques for denaturing double-stranded oligonucleotides include, but are not limited to, heating, adding a denaturing solution, adding salt, or changing the pH.

Oligonucleotides can be denatured through heat in a process that is similar to melting. Heat is applied until the oligonucleotide has unwound itself and separated into two single strands. Techniques for denaturing oligonucleotides with heat are well known to those of ordinary skill in the art. For example, denaturing may consist of heating the oligonucleotides to about 75-95° C., for about 5-20 minutes. Denaturing with heat may be performed by using a heater to heat the solution in contact with the substrate 202. In one implementation, resistors embedded in a microelectrode array may function as heaters to heat solution in contact with the surface of the microelectrode array. Alternatively, a heated solution is flowed across the surface of the substrate 202.

Oligonucleotides may also be denatured by the addition of a denaturing solution. A denaturing solution can include any one or more of various chemical agents such as formamide, guanidine, sodium salicylate, dimethyl sulfoxide (DMSO), propylene glycol, and urea. These chemical denaturing agents lower the melting temperature ($T_m$) by competing for hydrogen bond donors and acceptors with pre-existing nitrogenous base pairs. One implementation of a denaturing solution contains sodium hydroxide (NaOH). Thus, a denaturing solution may contain about 0.1-1 mol/L NaOH. NaOH increases the pH thereby removing the hydrogen-bonds-contributing protons from guanine and thymine, thus breaking the hydrogen bonds between the two oligonucleotide strands. Another implementation of a denaturing solution contains a 60% DMSO solution that is brought into contact with the oligonucleotides. DNA denaturing solutions are also available from multiple commercial suppliers such as a solution of 0.5 M NaOH with 1.5 M NaCl available from Avantor (Radnor, PA, USA).

In some implementations, the denaturing solution is brought into contact with the oligonucleotides for at least one minute. Techniques for denaturing oligonucleotides with denaturing buffers and denaturing solutions are well known to those of ordinary skill in the art. For a discussion of chemical denaturation techniques see Wang X, Lim H J, Son A. Characterization of denaturation and renaturation of DNA for DNA hybridization. *Environ Health Toxicol*. 2014: 29:e2014007.

A change in salt concentration can also denature oligonucleotides. A high concentration of salt will cause double-stranded oligonucleotides to denature. Thus, a salt solution may be used as a denaturing solution. Oligonucleotide denaturation with salts is similar to denaturation through the use of organic solvents. Salt is often used in addition to an acid for the full denaturation of oligonucleotides, and it may also be used in conjunction with heat. Salt may be combined with other chemicals such as isopropanol and ethanol to denature oligonucleotides. Techniques for denaturing oligonucleotides with salt are well known to those with ordinary skill in the art. See Gruenwedel D W, Hsu C H. Salt effects on the denaturation of DNA. *Biopolymers*. 1969: 7(4):557-70.

If the substrate 202 is implemented as a microelectrode array that contains multiple electrodes, activation of the electrodes may be used to increase or decrease the pH of the solution in contact with oligonucleotides and cause the double-stranded structures to denature. Double-stranded DNA may denature at a pH 5 are lower or a pH 9. The pH of the solution may be changed by redox reactions caused by the activation of electrodes in the microelectrode array. Electrodes other than those included in the microelectrode array may also be used to alter the pH of the solution.

Another technique for denaturation uses a change in the strength of hybridization or the binding energy between the oligonucleotide hairpin 100 and the anchor strand 204 following cleavage of the enzyme cleavage region 114. The binding energy is affected by multiple factors as understood by those ordinary skill in the art such as the length of the double-stranded structure 212, the ionic strength and pH of the solution in contact with oligonucleotides, and the sequence (e.g., G-C content). The binding energy of a hairpin or other double-stranded oligonucleotide can be estimated using software such as NUPACK.

Cleavage of the enzyme cleavage region 114 breaks the covalent connection between the remainder of the oligonucleotide that hairpin 210 and anchor strand 204. Thus, at Time 4 it is only hydrogen bonding between the "N" and "x*" regions that hold the remainder of the oligonucleotide hairpin 210 to the anchor strand 204. Regions of double-stranded oligonucleotide hybridization of less than about 10 or less than about 8 nucleotides generally undergo continuous association and disassociation. Thus, even if the double-stranded structure 212 between the remainder of the oligonucleotide hairpin 210 and anchor strand 204 is fully complementary, if it is less than about 10 nucleotides the remainder of the oligonucleotide hairpin 210 may spontaneously separate from the anchor strand 204 following action of the cleavage enzyme 208.

Time 5 is followed by a wash step with an aqueous solution such as a wash buffer. This washing removes the remainder of the first oligonucleotide hairpin 210A and the cleavage enzyme 208 from the solution in contact with the substrate 202. Removal of the remainder of the first oligonucleotide hairpin 210A prevents re-hybridize when the denaturing conditions stop. The wash step and denaturing may be combined by flowing a solution across the surface of the substrate 202 that both denatures oligonucleotides and washes away the remainder of the first oligonucleotide hairpin 210A. For example, a heated wash buffer (e.g., a standard DNA storage buffer) or a denaturing solution may be flowed across the substrate 202. In some implementations, the denaturing solution is heated.

FIG. 2B begins with Time 6 illustrating the anchor strand 204 now extended by the addition of the first payload region 112A (i.e., "x"). The process repeats by contacting the anchor strand 204 with a second oligonucleotide hairpin 100B. The second oligonucleotide hairpin 100B includes a second payload region 112B. The second payload region 112B may include different nucleotides than the first payload region 112A. For example, the first payload region 112A may include the nucleotides AT while the second payload region 112B includes the nucleotides GC. As a further example, the first payload region 112A may include a first piece of arbitrary information (e.g., a first bit) and the second payload region 112B may encode a second piece of arbitrary information (e.g., a second bit). However, it is also possible that the second payload region 112B contains the same nucleotides as the first payload region 112A.

The second overhang region 106B of the second oligonucleotide hairpin 100B may have a different sequence than the first overhang region 106A of the first oligonucleotide hairpin 100A. The second overhang region 106B hybridizes to an anchor strand 204 that ends with the sequence "x" which was formerly the first payload region 112A. Recall that the overhang region 106 may typically be about 3-4 nucleotides. Thus, in some implementations, if the first payload region 112A is at least about 3-4 nucleotides, the entirety of the sequence to which the second overhang region 106B hybridizes will be newly added to the anchor strand 204. In this implementation, the design of the second overhang region 106B is based on the sequence of the previously added first payload region 112A. However, in other implementations the second overhang region 106B may be the same as the first overhang region 106A. For example, if the sequence of anchor strand 204 is . . . CTCTCT . . . and the first payload region 112A has the sequence CT, then the addition of the first payload region 112A will not change the sequence at the end of the anchor strand 204.

To use the techniques of this disclosure to assemble oligonucleotides with any arbitrary sequence of nucleotides, there may need to be a collection of oligonucleotide hairpins containing a large number of different versions of the overhang region 106 to have a sequence that is fully complementary to the end of anchor strand 204. If, for example, the length of the overhang region 106 is 4 nucleotides and the end of that anchor strand 204 which it hybridizes may have any combination of the four canonical bases, then are $4^4$ or 256 possibilities for the sequence of the overhang region 106. To add any single nucleotide onto the end of an anchor strand 204 with any possible sequence of nucleotides, there would need to be 256 versions of each oligonucleotide hairpin 100 that includes one of the four canonical bases in the payload region 112. This would be a total of 1024 different oligonucleotide hairpin 100 sequences.

The number of different oligonucleotide hairpins 100 needed in a collection of oligonucleotide hairpins may be greatly reduced if the oligonucleotides are used to encode only two different pieces of arbitrary information such as the bits 0 and 1. Consider the example in which the bit 0 is encoded by AGCT, the bit 1 is encoded by GTCA, and the length of the overhang region 106 is 4 nucleotides. In this example, there are two different possibilities for the nucleotides in the payload region 112. This results in the final four nucleotides on the end of the anchor strand 204 being either AGCT or GTCA depending on which bit value was added last. Thus, two versions of the oligonucleotide hairpin 100 that encodes the bit 0 are needed: one in which the overhang region 106 is TCGA (complementary to AGCT) and one in which the overhang region is CAGT (complementary to GTCA). Similarly, there will be two versions of the oligonucleotide that hairpin 100 that encodes the bit 1. Thus, four different species of oligonucleotide hairpins 100 are sufficient to assemble an oligonucleotide encoding any arbitrary string of binary digits.

Time 7 illustrates the hybridization of the second oligonucleotide hairpin 100B to the anchor strand 204. As before, there is a nick in the backbone between the second payload region 112B and the end of anchor strand 204. Although the second overhang region 106B represented by "N" is illustrated in the example as hybridizing to the portion of the anchor strand 204 illustrated by "x" that came from the first payload region 112A, the length of the "N" region may extend beyond the "x" portion of anchor strand 204 and hybridize with one or more nucleotides of the original anchor strand 204 represented as "a".

Time 8 illustrates ligation of the second oligonucleotide hairpin 100B to the anchor strand 204. Operation of the ligase 206 may be the same as described above for Time 3. Following ligation, the second payload region 112B is covalently attached to the first payload region 112A at the end of the anchor strand 204.

Time 9 illustrates denaturing the double-stranded structure formed from the remainder of the second oligonucleotide hairpin 210B and the anchor strand 204. Operation of the cleavage enzyme 208 may be the same as described above for Time 4. However, a different cleavage enzyme may be used. This separates the second payload region 112B from the remainder of the second oligonucleotide hairpin 210B. At this point the anchor strand 204 is now extended by the addition of the nucleotides from the first payload region 112A (e.g., "x") and the second payload region 112B (e.g., "w").

Time 10 illustrates the separation of the remainder of the second oligonucleotide hairpin 210B from the anchor strand 204 following denaturation. Denaturation may be performed using any of the techniques discussed above for Time 5. The same or a different technique for denaturation may be used. This is followed by an additional washing step. The steps of FIG. 2 may be repeated multiple times with additional oligonucleotide hairpins 100 that each include an additional payload region 112. Continuation of this process appends additional nucleotides to the end of the anchor strand 204 creating an oligonucleotide with any arbitrary sequence on the surface of the substrate 202.

The techniques of this disclosure involve hybridization of single-stranded oligonucleotides either to form hairpins or to attach to anchor strands. The sequence of oligonucleotides or oligonucleotide regions that hybridize to each other may be complementary, but it is understood that they need not be 100% complementary. As used herein, the terms "complementary" or "complementarity" are used in reference to oligonucleotides related by the base-pairing rules. "Complementary" or "complementarity" refers to the nucleotides of a nucleic acid sequence that can bind to another nucleic acid sequence through hydrogen bonds, e.g., nucleotides that are capable of base pairing, e.g., by Watson-Crick base pairing or other base pairing. Nucleotides that can form base pairs, e.g., that are complementary to one another, are the pairs: cytosine and guanine, thymine and adenine, adenine and uracil, and guanine and uracil. Complementarity may be "partial," in which only some of the nucleic acids bases are matched according to the base-pairing rules. Or there may be "complete" or "total" complementarity between the nucleic acids. The degree of complementarity between oligonucleotides has significant effects on the efficiency and strength of hybridization between nucleic acid strands.

Oligonucleotide sequences that hybridize to each other may have, at least 50%, at least 60%, at least 70%, at least 80%, at least 90%, at least 95%, at least 99%, or 100% sequence complementarity. Percent complementarity between particular stretches of oligonucleotide sequences can be determined routinely using software such as the BLAST programs (basic local alignment search tools) and PowerBLAST programs known in the art (Altschul et al., J. Mol. Biol., 1990, 215, 403-410: Zhang and Madden, Genome Res., 1997, 7, 649-656) or by using the Gap program (Wisconsin Sequence Analysis Package, Version 8 for Unix, Genetics Computer Group, University Research Park, Madison Wis.), using default settings, which uses the algorithm of Smith and Waterman (Adv. Appl. Math., 1981, 2, 482-489).

As used herein, the term "hybridization" is used in reference to the pairing of complementary nucleic acids. Hybridization and the strength of hybridization (e.g., the strength of the association between the nucleic acids) is influenced by such factors as the degree of complementary between the nucleic acids, stringency of the conditions involved, and the $T_m$ of the formed hybrid. "Hybridization" methods involve the annealing of one nucleic acid to another, complementary nucleic acid, e.g., a nucleic acid having a complementary nucleotide sequence. The ability of two oligonucleotides comprising complementary sequences to find each other and anneal through base pairing interaction is a well-recognized phenomenon. The initial observations of the "hybridization" process by Marmur and Lane, *Proc. Natl. Acad. Sci. USA* 46:453 (1960) and Doty et al., *Proc. Natl. Acad. Sci. USA* 46:461 (1960), have been followed by the refinement of this process into an essential tool of modern biology.

As used herein, the term "$T_m$" is used in reference to the "melting temperature." The melting temperature is the temperature at which a population of double-stranded nucleic acid molecules becomes half dissociated into single strands. Several equations for calculating the $T_m$ of nucleic acids are well known in the art. As indicated by standard references, a simple estimate of the $T_m$ value may be calculated by the equation: $T_m=81.5+0.41*(\% \text{ G+C})$, when a nucleic acid is in an aqueous solution at 1 M NaCl (see, e.g., Anderson and Young, "Quantitative Filter Hybridization" in Nucleic Acid Hybridization (1985). Other references (e.g., Allawi and SantaLucia, Biochemistry 36:10581-94 (1997)) include more sophisticated computations which account for structural, environmental, and sequence characteristics to calculate $T_m$.

Unless otherwise specified, hybridization, as used throughout this disclosure, refers to the capacity for hybridization between two single-stranded oligonucleotides or oligonucleotide segments at 21° C., in 1×TAE buffer containing 40 mM TRIS base, 20 mM acetic acid, 1 mM ethylenediaminetetraacetic acid (EDTA), and 12.5 mM $MgCl_2$. Hybridization and washing conditions are well known and exemplified in Sambrook, J., Fritsch, E. F, and Maniatis, T. *Molecular Cloning: A Laboratory Manual.* Second Edition, Cold Spring Harbor Laboratory Press, Cold Spring Harbor (1989), particularly Chapter 11 and Table 11.1 therein; and also in Sambrook, J, and Russell, W., *Molecular Cloning: A Laboratory Manual.* Third Edition, Cold Spring Harbor Laboratory Press, Cold Spring Harbor (2001). As is known to those of ordinary skill in the art, conditions of temperature and ionic strength determine the "stringency" of the hybridization.

FIG. 3 shows a time series 300 that illustrates the use of a microelectrode array to control the location of oligonucleotide hairpin hybridization. The oligonucleotide hairpins 100 as well as the general technique the same as described above in FIGS. 1 and 2. The techniques of this disclosure can be used on an inert flat substrate or beads to create multiple oligonucleotides with the same sequence. However, some applications, such as DNA data storage, benefit from the ability to create oligonucleotides with different sequences. A microelectrode array may be used to synthesize multiple different oligonucleotides with separate sequences in parallel on a single substrate. The different oligonucleotides could, for example, encode binary data corresponding to multiple different computer files or multiple different genes, gene fragments, or probes.

The microelectrode array 302 shown in this time series 300 is illustrated with only three electrodes 304 but it is to be understood that the microelectrode array 302 may have many more electrodes 304. The microelectrode array 302 may contain a large number of microelectrodes that make it possible to create many different oligonucleotides (e.g., 10,000, 60,000, 90,000, or more) on the surface of a single array. This high level of multiplexing is made possible by the microelectrode density which may be approximately 1000 microelectrodes/cm², 10,000 microelectrodes/cm², or a different density. Examples of suitable microelectrode arrays are provided in Bo Bi et al., *Building Addressable Libraries: The Use of "Safety-Catch" Linkers on Microelectrode Arrays,* 132 J. Am. Chem. Soc. 17,405 (2010), Nguyen et al., Scaling DNA Data Storage with Nanoscale Electrode Wells, 14:7 Science Advances (2021), and in U.S. Pat. Pub. No. 2020/0384434.

The microelectrode array 302 includes a plurality of electrodes 304 that can be independently activated to vary the charge across the surface of the microelectrode array 302. In one example implementation, the microelectrode array 302 is functionalized by spin coating with a 3 wt % solution of agarose in 1×TBE buffer for 30 s at 1500 rpm. After coating, the microelectrode array 302 is baked at 50° C., for 1 h. This creates a surface with functional groups that can bind to the anchor strands 204. The anchor strands 204 may be synthesized directly onto the agarose coating using standard phosphoramidite reagents and methods.

At Time 1, the microelectrode array 302 is shown coated with anchor strands 204 represented as black bars. All of the anchor strands 204 on the microelectrode array 302 may have the same nucleotide sequence. Persons of ordinary skill in the art are aware of multiple ways to coat a microelectrode array 302 with single-stranded oligonucleotides. Techniques known to those of skill in the art for the generation of DNA microarrays may be adapted for this purpose. For example, the anchor strands 204 may be synthesized in situ using techniques such as those described in R. D. Egeland and E. M. Southern, Electrochemically directed synthesis of oligonucleotides for DNA microarray fabrication, *Nucleic Acids Research,* 2005 Vol. 33, No. 14. The surface of the microelectrode array 302 is covered with an aqueous solution that may be either an aqueous buffer solution or a mixed aqueous/organic solvent system. The aqueous solution in contact with the surface of the microelectrode array 302 is electrically conductive. The aqueous solution does not necessarily need buffering properties and may be a simple salt solution (e.g., 1 M NaCl).

Attachment of the anchor strands 204 to the surface of the microelectrode array 302 may not correlate in a one-to-one manner with the electrodes 304. Some electrodes 304 may have more than one anchor strand 204 attached. Some anchor strands 204 may be attached to a portion of the microelectrode array 302 that does not include an electrode 304. Some electrodes 304 may have no anchor strands 204 attached (not shown). However, all anchor strands 204 attached to the same electrode 304 will be exposed to the same electrochemical environment and generate the same oligonucleotides.

At Time 2, a first subset of the electrodes 304 is selectively activated. As used herein, "activation" of an electrode 304 refers to causing the electrode 304 to have a positive charge relative to a reference electrode or to ground. In some implementations the positive charge may be about 3.3 V. Persons of ordinary skill in the art will be able to readily identify an appropriate voltage based on the design of the microelectrode array 302 and the solution in contact with the surface of the microelectrode array 302.

Electrically controlled hybridization or electro-assisted hybridization uses electrodes on the microelectrode array 302 to create positive charges that electrostatically attract negatively charged oligonucleotide hairpins 100. This attraction pulls the oligonucleotide hairpins 100 to only those electrodes 304 that currently have a positive charge and creates a higher localized concentration of oligonucleotide hairpins 100 in the solution near each positively charged electrode 304. This both creates site-selectivity, causing reactions to occur only those electrodes 304 that are activated with a positive charge, and concentrates oligonucleotide hairpins 100 in the region of the active electrodes, leading to a higher local concentration which can increase reaction kinetics. Electrodes 304 that are negatively charged or neutral (i.e., no charge) do not attract the oligonucleotide hairpins 100.

At Time 2, a first oligonucleotide hairpin 100A hybridizes to the anchor strands 204 in the proximity of the activated electrodes 304. Although the first oligonucleotide hairpin 100A is present in solution across the entire surface of the microelectrode array 302, it hybridizes in appreciable amounts only to those anchor strands 204 attached to activated electrodes. There may be some minimal amount of hybridization to anchor strands 204 that are not attached to positively charged electrodes 304, but this will generally be undetectable and not affect the sequences of the vast majority of oligonucleotides. Hybridization results in a double-stranded oligonucleotide sequence as indicated by a series of black dots.

Subsequent steps are performed as described previously. The nick that remains in between the end of the anchor strand 204 and the first payload region 112A is closed by the activity of ligase. The ligase may be added at the same time as the first oligonucleotide hairpin 100A. Moreover, a current is maintained at the electrodes 304 at least during the addition of the ligase and a subsequent washing step. A cleavage enzyme is added which separates the first payload region 112A from the remainder of the first oligonucleotide hairpin. The remainder of the first oligonucleotide hairpin is washed away.

Time 3 illustrates the microelectrode array 302 after the first payload region 112A is added to the ends of the anchor strands 204 on the electrodes 304 activated Time 2. Electrodes 304 may be deactivated at this time. In this example, some of the anchor strands 204 remain as they were originally while others have been extended by the addition of one or more nucleotides provided by the first payload region 112A. Thus, the microelectrode array 302 is coated with a plurality of anchor strands 204 having multiple different sequences.

At Time 4, a second subset of electrodes is activated. The second subset of electrodes may be different than the first subset of electrodes. However, there may be some overlap between the two subsets and the same electrode 304 may be included in both subsets. A second oligonucleotide hairpin 100B is directed to hybridize with a different set of anchor strands 204 based on the change of the activated electrodes 304. Hybridization of the second oligonucleotide hairpin 100B is followed by ligation, digestion with a cleavage enzyme, and denaturation as described above.

Time 5 illustrates the microelectrode array 302 after the second payload region 112B is attached to the ends of anchor strands 204 on the electrodes 304 activated Time 4. In this example, the second payload region 112B has been added to the ends of some anchor strands 204 that were not previously extended and to some anchor strands 204 to which the first payload region 112A was added.

The oligonucleotide hairpins 100 that are available in solution to hybridize with the anchor strands 204 may be changed during each round of assembly as illustrated by the addition of the first oligonucleotide hairpin 100A at Time 2 and the second oligonucleotide hairpin 100B at Time 4. This controls "what" is added to the anchor strands 204 by controlling which payload region 112 is added. The selection of which electrodes 304 are activated controls "where" addition occurs. By varying the available oligonucleotide hairpins 100 and the activated electrodes 304, multiple oligonucleotides each with a different sequence of nucleotides can be assembled in parallel on the microelectrode array 302. The spatial addressability of hybridization provided by the microelectrode array 302 makes it possible to assemble at least a first oligonucleotide having a first arbitrary sequence at a first location on the substrate and a second oligonucleotide having a second arbitrary sequence a second location on the substrate.

Figure 4:
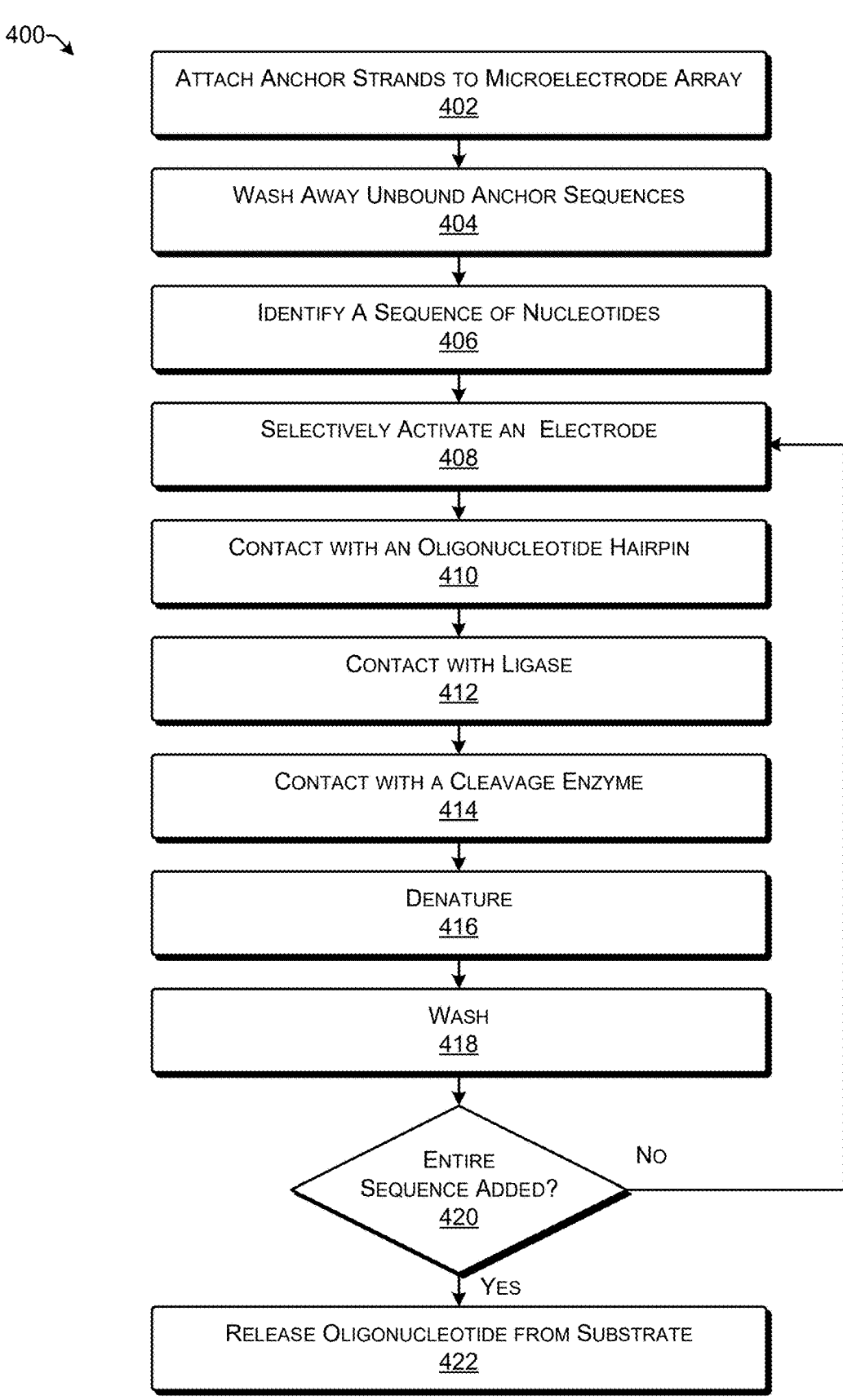
FIG. 4 is a flow diagram showing an illustrative process for assembling one or more oligonucleotides with sequences from oligonucleotide hairpins.

FIG. 4 shows a process 400 for assembling one or more oligonucleotides having arbitrary sequences from oligonucleotide hairpins. For ease of understanding, the process 400 is delineated as separate operations represented as independent blocks. However, unless otherwise contradicted by context, any number of the described process blocks may be combined to implement the process or an alternate process. Moreover, it is also possible that one or more of the provided operations is modified or omitted.

At operation 402, anchor strands are attached to a substrate. The substrate may be any type of substrate suitable for solid-phase synthesis of oligonucleotides such as silicon, glass, or plastic. The substrate may be a generally flat surface or the substrate may be a bead. In an implementation, the substrate may be a microelectrode array as described above. The anchor strands may be attached to the substrate by any conventional technique for attaching oligonucleotide sequences to a solid substrate. For example, the surface of the substrate may be coated with linker molecules that in turn attach to an end of the anchor strands. As a further example, the surface of the substrate may be functionalized through silanization or coating with agarose. This creates a substrate that is coated with a plurality of anchor strands.

At operation 404, unbound anchor strands are washed away. This removes any anchor strands that are not attached to the microelectrode array. This washing step may be performed with water or an aqueous wash buffer. In some implementations, operations 402 and 404 may be omitted. Thus, the process 400 may begin with a substrate that has been pre-coated with anchor strands.

At operation 406, an arbitrary sequence of nucleotides is identified. The process 400 will create one or more oligonucleotides having the sequence. In an implementation, the order the nucleotides may encode any type of arbitrary information including, but not limited to, a string of binary digits. Thus, operation 406 may be implemented by identifying a binary string to encode in the oligonucleotide. For example, the binary string may represent digital information such as a computer file. The identified sequence of nucleotides may be stored in a computer system that is used to control an automated system for assembling the oligonucleotides. If multiple oligonucleotides are being assembled in parallel, such as by use of a microelectrode array, multiple different sequences of nucleotides can be identified at operation 406.

At operation 408, if the substrate is a microelectrode array, a subset of electrodes in the microelectrode array is selectively activated. If the substrate is an inert substrate and not a microelectrode array, operation 408 will be omitted. The subset of electrodes includes at least one electrode. Activation of the electrode(s) applies a positive charge which electrostatically attracts negatively charged oligonucleotides to a specific location on the surface of the substrate. The specific location may be varied during each round of oligonucleotide hairpin addition by activating a different subset of electrodes. Oligonucleotide hairpins present in the solution are attracted to and hybridize with a subset of anchor strands attached to the activated electrodes. The electrodes may remain activated during some or all of the following operations 410-416.

In one implementation, a voltage of +3.3 V may be applied for three cycles of 60 s with 10 s at 0 V between each cycle. Without being bound by theory, this length and duration of activation may provide the oligonucleotide hairpins with sufficient time to migrate to the electrodes and hybridize to the anchor strands. Specific voltages and timings of the electrode activation will be varied based on the design of the microelectrode array and the concentration of oligonucleotide hairpins in solution. Persons of ordinary skill in the art will be able to readily identify appropriate modifications to the strength and timing of electrode activation.

At operation 410, an anchor strand attached to the substrate is contacted with an oligonucleotide hairpin under conditions such that an overhang region of the oligonucleotide hairpin hybridizes to the end of the anchor strand. The conditions suitable for hybridization of two single-stranded oligonucleotide sequences may be the conditions described above or conditions known to persons of ordinary skill in the art. As discussed above, hybridization does not require fully complementary sequences but only that the strength of attachment between the oligonucleotide hairpin and the anchor strands is sufficient to hold the oligonucleotide hairpin in place until the subsequent ligation step.

The oligonucleotide hairpin includes a loop region and a stem region. The stem region has an overhang side and a non-overhang side. An end of the overhang side of the stem region includes the overhang region. An end of the non-overhang side of the stem region includes a payload region. The payload region contains one or more nucleotides. The non-overhang side of the stem region also includes an enzyme cleavage region directly adjacent to the payload region. The enzyme cleavage region is cleaved by contact with a cleavage enzyme.

At operation 412, the oligonucleotide (i.e., the oligonucleotide hairpin hybridized to the anchor strand) is contacted with ligase under conditions such that the ligase catalyzes the formation of a phosphodiester bond between the payload region of the oligonucleotide hairpin and the anchor strand. In an implementation, operation 410 and operation 412 may be combined so that the oligonucleotide hairpins and the ligase are added at the same time. The use of ligase and suitable reaction conditions for joining 5'-end and 3'-end of two oligonucleotides are well known to those of ordinary skill in the art. The ligase is added in an appropriate buffer such as a ligase buffer that contains ATP. After addition of the ligase, the oligonucleotide hairpin is covalently attached to the end of the anchor strand. The hairpin structure remains. Following addition of the ligase, any unbound oligonucleotide hairpins, as well as excess ligase, may be washed away with a wash buffer. Thus, only those oligonucleotide hairpins that have been ligated to an anchor strand remain.

At operation 414, the oligonucleotide is contacted with the cleavage enzyme under conditions such that the cleavage enzyme cleaves the enzyme cleavage region thereby separating the payload region from the remainder of the oligonucleotide hairpin. The payload region remains covalently attached to the end of the anchor strand.

Many different types of cleavage enzymes capable of creating backbone nicks or removing entire nucleotides from double-stranded oligonucleotides are known to those of ordinary skill in the art. The enzyme cleavage region will be designed so that it has the sequence and type of nucleotides that are cleaved by the selected cleavage enzyme. The specific cleavage enzyme and the sequence of the enzyme cleavage region will be selected and designed so that the cleavage separates the payload region from the remainder of the oligonucleotide hairpin.

In one implementation, the enzyme cleavage region is a single uracil DNA and the cleavage enzyme comprises uracil DNA Glycosylase (UDG) and an endonuclease. In one implementation, the enzyme cleavage region is a single RNA nucleotide, the remainder of the oligomer that hairpin is DNA, and the cleavage enzyme comprises ribonuclease H. In one implementation, the enzyme cleavage region comprises a recognition site and cut site and the cleavage enzyme comprises a restriction enzyme that cleaves at the cut site. In one implementation, the enzyme cleavage region comprises a recognition site and cut site and the cleavage enzyme comprises a nicking enzyme that cleaves at the cut site.

At operation 416, the double-stranded structure formed from hybridization of the oligonucleotide hairpin to the anchor strand is denatured. This separates the oligonucleotide hairpin other than the payload region from the anchor strand. The payload region remains covalently attached to the end of the anchor strand. Denaturing may also open the hairpin in the oligonucleotide hairpin.

Denaturing may be performed by any suitable technique including, but not limited to, heating above the $T_m$ of the assembled double-stranded oligonucleotide, adding sodium hydroxide, adding a denaturing solution, changing the pH, and increasing the salt concentration. These and other techniques for denaturing double-stranded oligonucleotides are well-known to those of ordinary skill in the art. In one implementation, the pH may be changed by activating electrodes in a microelectrode array to cause a redox reaction in a solution contacting the surface of the microelectrode array that results in an increase or decrease of the pH to a level that denatures double-stranded oligonucleotides.

At operation 418, the surface of the microelectrode array or inert substrate is washed with a wash buffer to remove the remainder of oligonucleotide hairpins in solution as well as the cleavage enzyme. This washing step may be performed while the electrodes are still activated. Thus, in some implementations, the electrodes are turned off only after the solution covering the microelectrode array is cleared of any oligonucleotides that could potentially hybridize with the anchor strands.

At operation 420, it is determined if the entire sequence of nucleotides is added to the end of the anchor strand. This determination can be performed by comparing the nucleotides contained in the payload regions of the oligonucleotide hairpins added thus far to the target sequence of nucleotides. This determination may be made, for example, by a computer system controlling the automated assembly of the oligonucleotides.

If the oligonucleotide is created to encode arbitrary information, such as a binary string, operations 410-418 may be repeated adding during each round an oligonucleotide hairpin that encodes in the payload region a first bit or a second bit. The oligonucleotide hairpins are added in order based on the binary string so that the encoded value of the nucleotides in the oligonucleotide represents the binary string. Operation 420 may then include a determination that the entire binary string is encoded in the oligonucleotide.

If the full sequence of nucleotides (or the entire binary string) has not been added, then the process 400 proceeds along the "no" path and returns to operation 408 (or operation 410 if a microelectrode array is not used) where operations 410-418 are repeated with an additional oligonucleotide hairpin that includes an additional payload region. This process is repeated until an oligonucleotide with the desired sequence of nucleotides is created. During each round of addition, the overhang region of an oligonucleotide hairpin hybridizes to the nucleotides at the end of the anchor strand that were the payload regions of one or more previous oligonucleotide hairpins.

As mentioned above, the subset of electrodes that are activated on the microelectrode array may be altered during each round of addition. Repeated cycles of adding oligonucleotide hairpins and activating selected subsets of electrodes enable the parallel creation of multiple different oligonucleotides each with a different sequence of nucleotides.

Thus, by combining this technique with a microelectrode array as the substrate, it is possible to assemble at least a first oligonucleotide having a first arbitrary sequence at a first location on the substrate and a second oligonucleotide having a second arbitrary sequence at a second location on the substrate. If it is determined that the entire nucleotide sequence (or the entirety of multiple nucleotides sequences) has been added to the ends of one or more anchor strands, then the process 400 proceeds along the "yes" path to operation 422.

At operation 422, the oligonucleotide created by repeated addition of oligonucleotide hairpins is released from the substrate. The oligonucleotides are released from the substrate by cleaving the connection between the base of the anchor strand and the substrate. The specific techniques for doing so will depend on how the anchor strand is attached to the substrate. If the anchor strand is attached to the substrate by a linker, the linker may be cleaved using a technique suitable for the chemistry of the particular linker. Numerous techniques for separating oligonucleotides bound to a solid substrate are known to those of ordinary skill in the art. For example, techniques used in the field of DNA microarrays may be adapted for this purpose. All oligonucleotides attached to the surface of the substrate may be released in a single operation.

Following separation from the substrate, the oligonucleotide may be processed further such as, for example, by amplification with PCR. The PCR product may be stored for short or long term. Any arbitrary information encoded in the oligonucleotide may be later obtained by sequencing the oligonucleotide and/or PCR amplification products.

Figure 5:
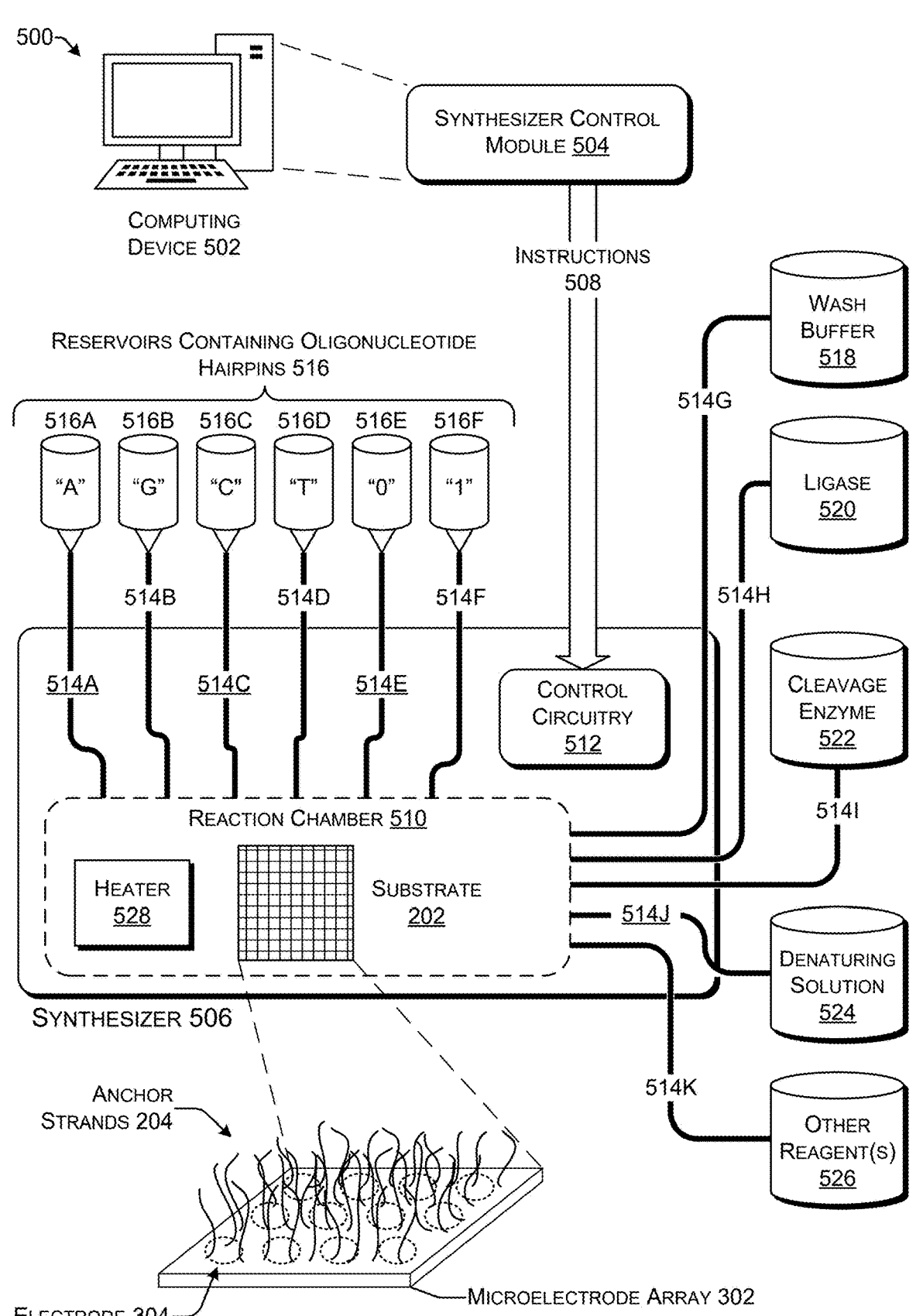
FIG. 5 is an illustrative system for creating oligonucleotides by implementing techniques of this disclosure.

FIG. 5 shows an illustrative system 500 that may include a computing device 502 with a synthesizer control module 504 that is communicatively connected to a synthesizer 506. The synthesizer control module 504 may provide instructions 508 that control the operation of the synthesizer 506. The instructions may cause the synthesizer 506 to create oligonucleotides with specific sequences and/or that encode specific arbitrary information. The computing device 502 may be implemented as any type of conventional computing device such as a desktop computer, a laptop computer, a server, a hand-held device, or the like. In an implementation, the computing device 502 may be a part of the synthesizer 506 rather than a separate device.

The synthesizer 506 is a device that selectively assembles oligonucleotide hairpins through hybridization to anchor strands 204 followed by ligation to the anchor strands and removal of portions of the oligonucleotide hairpins other than a payload region. Synthesis is performed on a substrate 202 coated with a plurality of anchor strands 204. The substrate may be implemented as a microelectrode array 302. The substrate 202 is located within a reaction chamber 510 or container capable of maintaining an aqueous or predominantly aqueous environment in contact with the surface of the substrate 202. Thus, the reaction chamber 510 is in fluid contact with the substrate 202. The substrate 202, whether implemented as a microelectrode array 302 or not, may be created in advance and placed within the reaction chamber 510.

Control circuitry 512 may control the operation of the synthesizer 506. The control circuitry 512 may be implemented as any type of circuitry suitable for controlling hardware devices such as a printed circuit board, microcontroller, programmable logic controller (PLC), or the like. The control circuitry 512 receives the instructions 508 provided by the synthesizer control module 504. Instructions 508 may indicate the order of payload regions that are to be assembled at individual electrodes 304 on the microelectrode array 302.

The control circuitry 512 may also be configured to selectively activate individual electrodes 304 in the microelectrode array 302 with a voltage sufficient to attract oligonucleotide hairpins to the substrate. If the synthesizer 506 is implemented with a microelectrode array 302, the control circuitry 512 can be configured to cause, through selective activation of individual electrodes 304 in the microelectrode array 302, the system 500 to assemble at least a first oligonucleotide with the first nucleotide sequence at a first location on the substrate 202 and a second oligonucleotide with a second nucleotide sequence at a second location on the substrate 202. In typical applications, thousands or millions of different oligonucleotides can be assembled on the surface of the microelectrode array 302.

The control circuitry 512 may also be able to activate fluid delivery pathways 514 that control movement of fluids throughout the synthesizer 506 including into the reaction chamber 510. The fluid delivery pathways 514 may be implemented by tubes and pumps, microfluidics, laboratory robotics, or other techniques known to those of ordinary skill in the art for moving fluids.

For example, microfluidic technology facilitates the automation of chemical and biological protocols. These devices manipulate small quantities of liquid at smaller scales and with higher precision than humans. Digital microfluidic (DMF) technology is one type of flexible microfluidic technology. DMF devices manipulate individual droplets of liquids on a grid of electrodes, taking advantage of a phenomenon called electrowetting on dielectric. Activating electrodes in certain patterns can move, mix, or split droplets anywhere on the chip. Microfluidics also includes full-stack microfluidics which are programmable systems that allow the unrestricted combination of computation and fluidics. Examples of microfluidic technology may be found in Willsey et al., *Puddle: A dynamic, error-correcting, full-stack microfluidics platform*, Aplos'19. April 13-17, 183 (2019).

In an implementation, the synthesizer 506 may include multiple reservoirs containing oligonucleotides and other reagents used by the synthesizer 506. The synthesizer 506 may include a set of reservoirs 516 containing different versions or species of oligonucleotide hairpins. The oligonucleotide hairpins may be any of the oligonucleotide hairpins described in this disclosure. Each unique species of oligonucleotide hairpin may be stored in a separate reservoir 516A-F. Thus, the synthesizer 506 may include at least a first reservoir 516A containing a first oligonucleotide hairpin, a second reservoir 516B containing a second oligonucleotide hairpin, a third reservoir 516C containing a third oligonucleotide hairpin, and a fourth reservoir 516D containing a fourth oligonucleotide hairpin. The synthesizer 506 may include a greater or lesser number of reservoirs containing oligonucleotide hairpins 516 than illustrated in FIG. 5. Each of the reservoirs 516A, 516B, 516C, 516D, 516E, 516F containing a species of oligonucleotide hairpin may have a separate fluid delivery pathway 514A, 514B. 514C. 514D, 514E, 514F configured to move the respective oligonucleotide hairpins into the reaction chamber 510.

As described above, each of the oligonucleotide hairpins includes a loop region and a stem region that has an overhang side and a non-overhang side. An end of the overhang side includes an overhang region that hybridizes to an anchor strand and an end of the non-overhang side includes a payload region. In an implementation, the oligonucleotide hairpins in a first reservoir 516A have a payload region that is the single nucleotide A, the oligonucleotide hairpins in a second reservoir 516B have a payload region that is the single nucleotide G, the oligonucleotide hairpins in a third reservoir 516C have a payload region that is the single nucleotide C, and the oligonucleotide hairpins in a fourth reservoir 516D have a payload region that is the single nucleotide T. In an implementation, the oligonucleotide hairpins in a first reservoir 516E have a payload region that encodes a first binary digit (e.g., 0) and the oligonucleotide hairpins in a second reservoir 516F have a payload region that encodes encode a second binary digit (e.g., 1). Oligonucleotide hairpins with the same payload region but different sequences for the overhang region may be combined in a single reservoir.

The oligonucleotide hairpins the reservoirs 516 may be pre-made using any oligonucleotide synthesis technique such as phosphoramidite synthesis or cloning in bacteria. The oligonucleotide hairpins may be stored in the reservoirs 516 where they are available to be transferred by fluid delivery pathways 514 to the reaction chamber 510. The oligonucleotide hairpins in the reservoirs 516 may be stored in an aqueous solution that uses a standard buffer for storing oligonucleotides. The concentration of oligonucleotide hairpins in the reservoirs 516 may be, for example, about 0.5, 1, 2, 3, 4, 5, 10, 15, 20, 30, or 50 nM.

One or more of a wash buffer reservoir 518, ligase reservoir 520, cleavage enzyme reservoir 522, denaturing solution reservoir 524, and reservoir for other reagent(s) 526 may also be connected by respective fluid delivery pathways 514G, 514H, 514I, 514J, 514K that are configured to deliver the respective reagents to the reaction chamber 510. The wash buffer reservoir 518 may include any wash buffer suitable for washing or manipulating oligonucleotides such as TE, TAE, and TBE. The wash buffer may be an aqueous buffer solution or mixed aqueous/organic solvent. Examples of organic solvents that may be added to a wash buffer include polar, miscible organic cosolvents (e.g., DMSO, acetonitrile, etc.) which may help remove metal ions, organic residues, and denatured protein.

The ligase reservoir 520 may include DNA ligase and/or RNA ligase in appropriate buffer and concentration for use in closing nicks in oligonucleotides within the reaction chamber 510. The cleavage enzyme reservoir 522 may contain any of the cleavage enzymes discussed in this disclosure such as UDG, RNase H, a nicking enzyme, or a restriction enzyme at an appropriate concentration in an appropriate buffer to cleave payload regions from the oligonucleotide hairpins. The denaturing solution reservoir 524 may provide any type of denaturing buffer or other denaturing solution (e.g., high salt, acid, or base) that can denature double-stranded oligonucleotides. There may also be one or more reservoirs for other reagent(s) 526 that contain reagents such as intercalating fluorescent dyes used to detect double-stranded oligonucleotides.

The synthesizer 506 also includes a means for denaturing double-stranded oligonucleotides in the reaction chamber 510. The means for denaturing double-stranded oligonucleotides may be implemented as a heater 528 configured to heat fluid in the reaction chamber above a temperature ($T_m$) in which double-stranded oligonucleotides denature. For example, this may be a temperature of about 75-95° C. The heater 528 may be implemented as part of the microelectrode array 302 such as resistive elements embedded underneath the electrodes. Application of current to the resistive elements is used to raise the temperature of solution inside the reaction chamber 510 causing double-stranded oligonucleotides to denature.

The means for denaturing double-stranded oligonucleotides may be one or more electrodes configured to change the pH of the solution in the reaction chamber 510 to the pH at which double-stranded oligonucleotides denature. Activation of the electrodes and generation of electrons at the electrode surfaces causes redox reactions in the solution within the reaction chamber 510 resulting in a change in pH.

Double-stranded oligonucleotides generally denature at pH below 5 or above 9. The electrodes that cause a change in the pH may be the electrodes 304 of the microelectrode array 302 or different electrodes. Thus, in one implementation, the means for denaturing double-stranded oligonucleotides is the microelectrode array 302.

In an implementation, the means for denaturing double-stranded oligonucleotides is the fluid delivery pathway 514J and the denaturing solution reservoir 524 configured to introduce the denaturing solution into the reaction chamber 510. The denaturing solution may be a commercial denaturing buffer or other solution (including solutions that do not provide buffering effects) such as a high salt solution, an acid, or a base as sufficient concentrations in quantities to denature double-stranded oligonucleotides in the reaction chamber 510.

The means for denaturing the double-stranded oligonucleotides may alternatively be implemented as the fluid delivery pathway 514G configured to introduce the wash buffer into the reaction chamber 510 and the wash buffer reservoir 518. In this implementation, the wash buffer is heated above a temperature at which double-stranded oligonucleotides denature. Thus, the wash buffer may be heated to a temperature of about 75-95° C. The heated wash buffer may be flowed through the reaction chamber 510 denaturing double-stranded oligonucleotides and washing unbound oligonucleotides from the reaction chamber 510 in a single step.

Additionally, the means for denaturing the double-stranded oligonucleotides may be spontaneous separation of an oligonucleotide hairpin from an anchor strand following cleavage of the enzyme cleavage region. Hybridization between an oligonucleotide hairpin and an anchor strand may be destabilized once the cleavage enzyme creates a nick in the backbone or removes a nucleotide from the enzyme cleavage region. Loss of the covalent connection may make the hybridization unstable and result in the remainder of the oligonucleotide hairpin spontaneously disassociating from the anchor strand. Because the remainder of the oligonucleotide hairpin separates from the anchor strand, flowing of a wash buffer or other solution over the surface of the substrate 202 can remove the remainder of the oligonucleotide hairpin from the reaction chamber 510 without heat or a denaturing solution.

The control circuitry 512 may be configured to selectively open the various fluid delivery pathways 514A-K in response to instructions 508 indicating an order of nucleotides in an arbitrary sequence. Thus, the control circuitry 512 can control the order and sequence that contents of the reservoirs containing oligonucleotide hairpins 516 are added to the reaction chamber 510. This in turn controls the order that various payload regions, with the corresponding nucleotides, are added to the end of an anchor strand 204. The control circuitry 512 is also configured to selectively activate the means of denaturing double-stranded oligonucleotides. Additionally, the control circuitry 512 may control the addition of other reagents such as ligase, a cleavage enzyme, a denaturing solution, and a wash buffer. For example, the control circuitry 512 may open the fluid delivery pathways 514A-K in an order that implements a process such as the process 400 illustrated in FIG. 4 or a similar process.

Illustrative Computer Architecture

Figure 6:
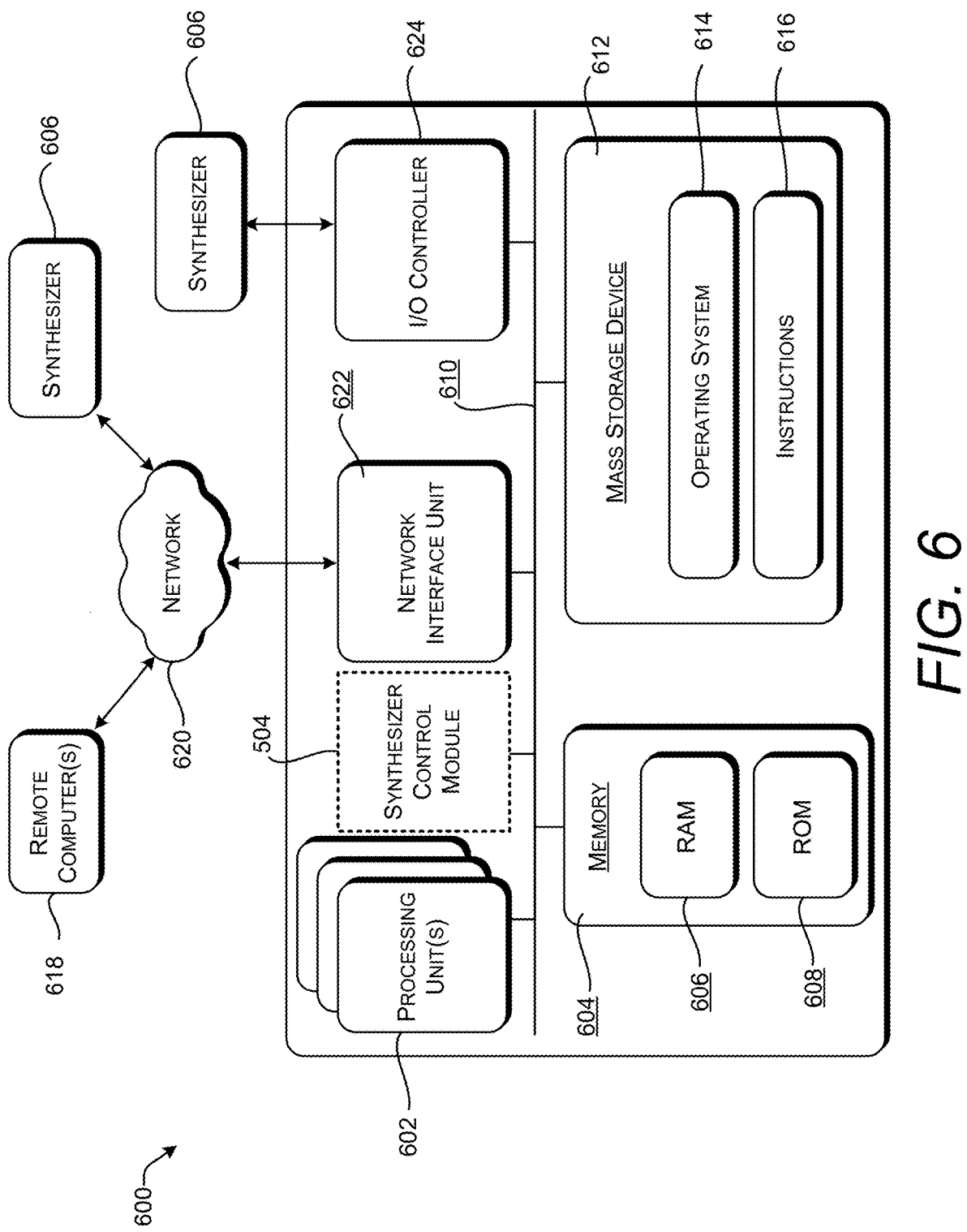
FIG. 6 is an illustrative computer architecture for implementing techniques of this disclosure.

FIG. 6 is a computer architecture diagram showing an illustrative computer hardware and software architecture for a computing device such as the computing device 502 introduced FIG. 5. In particular, the computer 600 illustrated in FIG. 6 can be utilized to implement the synthesizer control module 504.

The computer 600 includes one or more processing units 602, a system memory 604, including a random-access memory 606 ("RAM") and a read-only memory ("ROM") 608, and a system bus 610 that couples the memory 604 to the processing unit(s) 602. A basic input/output system ("BIOS" or "firmware") containing the basic routines that help to transfer information between elements within the computer 600, such as during startup, can be stored in the ROM 608. The computer 600 further includes a mass storage device 612 for storing an operating system 614 and other instructions 616 that represent application programs and/or other types of programs such as, for example, instructions to implement the synthesizer control module 504. The mass storage device 612 can also be configured to store files, documents, and data.

The mass storage device 612 is connected to the processing unit(s) 602 through a mass storage controller (not shown) connected to the system bus 610. The mass storage device 612 and its associated computer-readable media provide non-volatile storage for the computer 600. Although the description of computer-readable media contained herein refers to a mass storage device, such as a hard disk, CD-ROM drive, DVD-ROM drive, or USB storage key, it should be appreciated by those skilled in the art that computer-readable media can be any available computer-readable storage media or communication media that can be accessed by the computer 600.

Communication media includes computer-readable instructions, data structures, program modules, or other data in a modulated data signal such as a carrier wave or other transport mechanism and includes any delivery media. The term "modulated data signal" means a signal that has one or more of its characteristics changed or set in a manner so as to encode information in the signal. By way of example, and not limitation, communication media includes wired media such as a wired network or direct-wired connection, and wireless media such as acoustic, radio frequency, infrared, and other wireless media. Combinations of any of the above should also be included within the scope of computer-readable media.

By way of example, and not limitation, computer-readable storage media can include volatile and non-volatile, removable and non-removable media implemented in any method or technology for storage of information such as computer-readable instructions, data structures, program modules, or other data. For example, computer-readable storage media includes, but is not limited to, RAM 606, ROM 608, EPROM, EEPROM, flash memory or other solid-state memory technology, CD-ROM, digital versatile disks ("DVD"), HD-DVD, BLU-RAY, 4K Ultra BLU-RAY, or other optical storage, magnetic cassettes, magnetic tape, magnetic disk storage or other magnetic storage devices, or any other medium that can be used to store the desired information and which can be accessed by the computer 600. For purposes of the claims, the phrase "computer-readable storage medium." and variations thereof, does not include waves or signals per se or communication media.

According to various configurations, the computer 600 can operate in a networked environment using logical connections to a remote computer(s) 618 through a network 620. The computer 600 can connect to the network 620 through a network interface unit 622 connected to the system bus 610. It should be appreciated that the network interface unit 622 can also be utilized to connect to other types of networks and remote computer systems. The computer 600 can also include an input/output controller 624 for receiving and processing input from a number of other devices, including a keyboard, mouse, touch input, an electronic stylus (not shown), or equipment such as a synthesizer 506 for synthesizing oligonucleotides. Similarly, the input/output controller 624 can provide output to a display screen or other type of output device (not shown).

It should be appreciated that the software components described herein, when loaded into the processing unit(s) 602 and executed, can transform the processing unit(s) 602 and the overall computer 600 from a general-purpose computing device into a special-purpose computing device customized to facilitate the functionality presented herein. The processing unit(s) 602 can be constructed from any number of transistors or other discrete circuit elements, which can individually or collectively assume any number of states. More specifically, the processing unit(s) 602 can operate as a finite-state machine, in response to executable instructions contained within the software modules disclosed herein. These computer-executable instructions can transform the processing unit(s) 602 by specifying how the processing unit(s) 602 transitions between states, thereby transforming the transistors or other discrete hardware elements constituting the processing unit(s) 602.

Encoding the software modules presented herein can also transform the physical structure of the computer-readable media presented herein. The specific transformation of physical structure depends on various factors, in different implementations of this description. Examples of such factors include, but are not limited to, the technology used to implement the computer-readable media, whether the computer-readable media is characterized as primary or secondary storage, and the like. For example, if the computer-readable media is implemented as semiconductor-based memory, the software disclosed herein can be encoded on the computer-readable media by transforming the physical state of the semiconductor memory. For instance, the software can transform the state of transistors, capacitors, or other discrete circuit elements constituting the semiconductor memory. The software can also transform the physical state of such components to store data thereupon.

As another example, the computer-readable media disclosed herein can be implemented using magnetic or optical technology. In such implementations, the software presented herein can transform the physical state of magnetic or optical media, when the software is encoded therein. These transformations can include altering the magnetic characteristics of particular locations within given magnetic media. These transformations can also include altering the physical features or characteristics of particular locations within given optical media, to change the optical characteristics of those locations. Other transformations of physical media are possible without departing from the scope and spirit of the present description, with the foregoing examples provided only to facilitate this discussion.

In light of the above, it should be appreciated that many types of physical transformations take place in the computer 600 to store and execute the software components presented herein. It also should be appreciated that the architecture shown in FIG. 6 for the computer 600, or a similar architecture, can be utilized to implement many types of computing devices such as desktop computers, notebook computers, servers, supercomputers, gaming devices, tablet computers, and other types of computing devices known to those skilled in the art. For example, the computer 600 may be wholly or partially integrated into the synthesizer 506. It is also contemplated that the computer 600 might not include all of the components shown in FIG. 6, can include other components that are not explicitly shown in FIG. 6, or can utilize an architecture completely different than that shown in FIG. 6.

ILLUSTRATIVE EMBODIMENTS

The following clauses described multiple possible embodiments for implementing the features described in this disclosure. The various embodiments described herein are not limiting nor is every feature from any given embodiment required to be present in another embodiment. Any two or more of the embodiments may be combined together unless context clearly indicates otherwise. As used herein in this document "or" means and/or. For example, "A or B" means A without B. B without A, or A and B. As used herein, "comprising" means including all listed features and potentially including addition of other features that are not listed. "Consisting essentially of" means including the listed features and those additional features that do not materially affect the basic and novel characteristics of the listed features. "Consisting of" means only the listed features to the exclusion of any feature not listed.

Embodiment 1. A method of assembling an oligonucleotide having an arbitrary sequence, the method comprising: a. contacting an anchor strand (204) attached to a substrate (202) with an oligonucleotide hairpin (100) under conditions such that an overhang region (106) of the oligonucleotide hairpin (100) hybridizes to the anchor strand (204), the oligonucleotide hairpin (100) comprising: a loop region (102); and a stem region (104) having an overhang side (108) and a non-overhang side (110), wherein an end of the overhang side includes the overhang region (106), an end of the non-overhang side includes a payload region (112), and the non-overhang side (110) includes an enzyme cleavage region (114) directly adjacent to the payload region (112), the enzyme cleavage region (114) cleaved by contact with a cleavage enzyme (208); b. contacting the oligonucleotide with ligase (206) under conditions such that the ligase (206) catalyzes the formation of a phosphodiester bond between the payload region (112) of the oligonucleotide hairpin and the anchor strand (204); c. contacting the oligonucleotide with the cleavage enzyme (208) under conditions such that the cleavage enzyme (208) cleaves the enzyme cleavage region (114) thereby separating the payload region (112) from a remainder of the oligonucleotide hairpin (210) and the payload region (112) remains attached to the anchor strand (204); d. denaturing a double-stranded structure (212) formed from hybridization of the oligonucleotide hairpin (100) to the anchor strand (204); and e. washing the oligonucleotide following the denaturing to remove the remainder of the oligonucleotide hairpin (210)).

Embodiment 2. The method of embodiment 1, further comprising repeating steps a-e with an additional oligonucleotide hairpin that includes an additional payload region.

Embodiment 3. The method of any of embodiments 1-2, further comprising: identifying a binary string to encode in the oligonucleotide; repeating steps a-e adding during each round an oligonucleotide hairpin that encodes in the payload region a first bit or a second bit, the oligonucleotide hairpins added in an order based on the binary string; determining that the binary string is encoded in the oligonucleotide; and releasing the oligonucleotide from the substrate.

Embodiment 4. The method of any of embodiments 1-3, wherein the enzyme cleavage region is a single uracil DNA and the cleavage enzyme comprises uracil DNA Glycosylase (UDG) and an endonuclease.

Embodiment 5. The method any of embodiments 1-3, wherein the enzyme cleavage region is a single RNA nucleotide and the cleavage enzyme comprises ribonuclease H.

Embodiment 6. The method of any of embodiments 1-3, wherein the enzyme cleavage region comprises a recognition site and cut site and the cleavage enzyme comprises a restriction enzyme or a nicking enzyme that cleaves at the cut site.

Embodiment 7. The method of any of embodiments 1-6, wherein the substrate comprises a microelectrode array (302) and the method further comprises selectively activating at least one electrode (304) in the microelectrode array (302) to electrostatically attract the oligonucleotide hairpin to a specific location on the substrate.

Embodiment 8. The method of embodiment 7, further comprising assembling a first oligonucleotide having a first arbitrary sequence at a first location on the substrate and assembling a second oligonucleotide having a second arbitrary sequence a second location on the substrate.

Embodiment 9. A collection of oligonucleotide hairpins comprising: a first oligonucleotide hairpin (100A) comprising a first loop region (102A) and a first stem region (104A), the first stem region (104A) having a first overhang side (108A) and a first non-overhang side (110A), wherein an end of the first overhang side (108A) includes a first overhang region (106A), an end of the first non-overhang side includes a first payload region (112A), and the first non-overhang side (110A) includes a first enzyme cleavage region (114A) directly adjacent to the first payload region (112A); and a second oligonucleotide hairpin (100B) comprising a second loop region (102B) and a second stem region (104B), the second stem region (104B) having a second overhang side (108B) and a second non-overhang side (110B), wherein an end of the second overhang side includes a second overhang region (106B), an end of the second non-overhang side includes a second payload region (112B), and the first non-overhang side (110B) includes a second enzyme cleavage region (114B) directly adjacent to the second payload region 112(B).

Embodiment 10. The collection of oligonucleotide hairpins of embodiment 9, wherein a length of the first payload region and a length of the second payload region are both the same and both 1 nucleotide or 2 nucleotides.

Embodiment 11. The collection of oligonucleotide hairpins of any of embodiments 9-10, wherein the first payload region encodes a first arbitrary information (e.g., a bit) and the second payload region encodes a second arbitrary information (e.g., a second bit).

Embodiment 12. The collection of oligonucleotide hairpins of any of embodiments 9-11, wherein the first payload region and the second payload region are each independently 2-5 nucleotides.

Embodiment 13. The collection of oligonucleotide hairpins of any of embodiments 9-12, wherein a length of the first overhang region and a length of the second overhang region are each at least 3 nucleotides.

Embodiment 14. The collection of oligonucleotide hairpins of any of embodiments 9-13, wherein the first stem region and the second stem region each include a stem stability region having a length such that a length of the stem region is at least 6 nucleotides.

Embodiment 15. A system (500) for assembling an oligonucleotide with an arbitrary sequence, the system comprising: a substrate (202) coated with a plurality of anchor strands (204): a reaction chamber (510) in fluid contact with the substrate (202): a first fluid delivery pathway (514A) configured to introduce into the reaction chamber (510) a first oligonucleotide hairpin (102A) comprising a first payload region (112A): a second fluid delivery pathway (514B) configured to introduce into the reaction chamber (510) a second oligonucleotide hairpin (100B) comprising a second payload region (112B): a third fluid delivery pathway (514H) configured to introduce ligase (206) into the reaction chamber (510): a fourth fluid delivery pathway (514I) configured to introduce a cleavage enzyme (208) that cleaves payload regions (112) from oligonucleotide hairpins (100): a fifth fluid delivery pathway (514G) configured introduce a wash buffer into the reaction chamber (510); means for denaturing double-stranded oligonucleotides; and control circuitry (512) configured to selectively open the first fluid delivery pathway (514A), the second fluid delivery pathway (514B), the third fluid delivery pathway (514H), the fourth fluid delivery pathway (514I), and the fifth fluid delivery pathway (514G) and to activate the means for denaturing double-stranded oligonucleotides in response to instructions (508) indicating an order of nucleotides in the arbitrary sequence.

Embodiment 16. The system of embodiment 15, wherein the means for denaturing double-stranded oligonucleotides is: the fifth fluid delivery pathway configured introduce the wash buffer into the reaction chamber and a reservoir containing the wash buffer, wherein the wash buffer is heated above a temperature at which double-stranded oligonucleotides denature; a sixth fluid delivery pathway (514J) configured to introduce a denaturing solution into the reaction chamber and a reservoir containing the denaturing solution; a heater (528) configured to heat fluid in the reaction chamber above a temperature at which double-stranded oligonucleotides denature; one or more electrodes (304) configured to change a pH of solution in the reaction chamber to a pH at which double-stranded oligonucleotides denature; or spontaneous denaturation following cleavage of a cleavage region in the first oligonucleotide hairpin or the second oligonucleotide hairpin.

Embodiment 17. The system of any of embodiments 15-16, further comprising: a sixth fluid delivery pathway (514C) configured to introduce into the reaction chamber a third oligonucleotide hairpin comprising a third payload region; and a seventh fluid delivery pathway (514D) configured to introduce into the reaction chamber a fourth oligonucleotide hairpin comprising a fourth payload region; wherein the first payload region is a single adenine nucleotide (A), the second payload region is a single guanine nucleotide (G), the third payload region is a single cytosine nucleotide (C), and the fourth payload region is a single thiamine nucleotide (T) or a single uracil nucleotide (U).

Embodiment 18. The system of any of embodiments 15-17, further comprising: a first reservoir containing the first oligonucleotide hairpin (516A), wherein the first oligonucleotide hairpin comprises a loop region and a stem region having an overhang side and a non-overhang side, wherein an end of the overhang side includes an overhang region that hybridizes to a one of the plurality of anchor strands and an end of the non-overhang side includes the first pay load region; and a second reservoir containing the second oligonucleotide hairpin (516B), wherein the second oligonucleotide hairpin comprises a second loop region and a second stem region having a second overhang side and a second non-overhang side, wherein an end of the second overhang side includes a second overhang region that hybridizes to a one of the plurality of anchor strands and an end of the second non-overhang side includes the second payload region.

Embodiment 19. The system of any of embodiments 15-18, wherein the substrate is a microelectrode array (302) and the control circuitry is further configured to selectively activate individual electrodes (304) in the microelectrode array with a voltage sufficient to attract oligonucleotide hairpins to the substrate.

Embodiment 20. The system of embodiment 19, wherein the control circuitry is configured to cause, through selective activation of individual electrodes in the microelectrode array, assembly of a first oligonucleotide with a first nucleotide sequence at a first location on the substrate and a second oligonucleotide with a second nucleotide sequence at a second location on the substrate.

CONCLUSION

Although the subject matter has been described in language specific to structural features and/or methodological acts, it is to be understood that the subject matter defined in the appended claims is not necessarily limited to the specific features or acts described above. Rather, the specific features and acts are disclosed as example forms of implementing the claims.

The terms "a," "an," "the" and similar referents used in the context of describing the invention are to be construed to cover both the singular and the plural unless otherwise indicated herein or clearly contradicted by context. The terms "based on," "based upon," and similar referents are to be construed as meaning "based at least in part" which includes being "based in part" and "based in whole," unless otherwise indicated or clearly contradicted by context. The terms "portion," "part," or similar referents are to be construed as meaning at least a portion or part of the whole including up to the entire noun referenced. As used herein, "approximately" or "about" or similar referents denote a range of ±10% of the stated value.

Certain embodiments are described herein, including the best mode known to the inventors for carrying out the invention. Of course, variations on these described embodiments will become apparent to those of ordinary skill in the art upon reading the foregoing description. Skilled artisans will know how to employ such variations as appropriate, and the embodiments disclosed herein may be practiced otherwise than specifically described. Accordingly, all modifications and equivalents of the subject matter recited in the claims appended hereto are included within the scope of this disclosure. Moreover, any combination of the above-described elements in all possible variations thereof is encompassed by the invention unless otherwise indicated herein or otherwise clearly contradicted by context.

Furthermore, references have been made to publications, patents and/or patent applications throughout this specification. Each of the cited references is individually incorporated herein by reference for its particular cited teachings as well as for all that it discloses.

The invention claimed is:

1. A method of assembling an oligonucleotide having an arbitrary sequence, the method comprising:
   identifying a binary string to encode in the oligonucleotide;
   a. contacting an anchor strand attached to a substrate with an oligonucleotide hairpin under conditions such that an overhang region of the oligonucleotide hairpin hybridizes to the anchor strand, the oligonucleotide hairpin comprising:
      a loop region; and
      a stem region having an overhang side and a non-overhang side, wherein an end of the overhang side includes the overhang region, an end of the non-overhang side includes a payload region, and the non-overhang side includes an enzyme cleavage region directly adjacent to the payload region, the enzyme cleavage region cleaved by contact with a cleavage enzyme;
   b. contacting the oligonucleotide with ligase under conditions such that the ligase catalyzes formation of a phosphodiester bond between the payload region of the oligonucleotide hairpin and the anchor strand;
   c. contacting the oligonucleotide with the cleavage enzyme under conditions such that the cleavage enzyme cleaves the enzyme cleavage region thereby separating the payload region from a remainder of the oligonucleotide hairpin and the payload region remains attached to the anchor strand;
   d. denaturing a double-stranded structure formed from hybridization of the oligonucleotide hairpin to the anchor strand;
   e. washing the oligonucleotide following the denaturing to remove the remainder of the oligonucleotide hairpin; and
   repeating steps a-e adding during each round an oligonucleotide hairpin that encodes in the payload region a first bit or a second bit, the oligonucleotide hairpins added in an order based on the binary string, wherein there are only four species of oligonucleotide hairpins and the oligonucleotide hairpin added in each round is selected based on a bit to be encoded and the payload region of the oligonucleotide hairpin added immediately prior so that an overhang region of the added oligonucleotide hairpin is complementary to the payload region of the oligonucleotide hairpin added immediately prior.

2. The method of claim 1, further comprising repeating steps a-e with an additional oligonucleotide hairpin that includes an additional payload region.

3. The method of claim 1, further comprising:
   determining that the binary string is encoded in the oligonucleotide; and
   releasing the oligonucleotide from the substrate.

4. The method of claim 1, wherein the enzyme cleavage region is a single uracil DNA and the cleavage enzyme comprises uracil DNA Glycosylase (UDG) and an endonuclease.

5. The method of claim 1, wherein the enzyme cleavage region is a single RNA nucleotide and the cleavage enzyme comprises ribonuclease H.

6. The method of claim 1, wherein the enzyme cleavage region comprises a recognition site and cut site and the cleavage enzyme comprises a restriction enzyme or a nicking enzyme that cleaves at the cut site.

7. The method of claim 1, wherein the substrate comprises a microelectrode array comprising a plurality of individually addressable electrodes.

8. The method of claim 7, further comprising assembling a first oligonucleotide having a first arbitrary sequence at a first location on the substrate and assembling a second oligonucleotide having a second arbitrary sequence a second location on the substrate.

9. The method of claim 7, wherein the method further comprises selectively activating at least one electrode in the microelectrode array to electrostatically attract the oligonucleotide hairpin to a specific location on the substrate.

10. The method of claim 8, wherein the first arbitrary sequence and the second arbitrary sequence are different and each encodes different arbitrary information.

11. The method of claim 1, wherein a length of the payload region is 2-5 nucleotides.

12. The method of claim 1, wherein a length of the payload region is 1 nucleotide or 2 nucleotides.

13. The method of claim 1, wherein a length of the overhang region is at least 3 nucleotides.

14. The method of claim 1, wherein the overhang region is fully complementary to the anchor strand.

15. The method of claim 1, wherein the stem region includes a stem stability region having a length such that a length of the stem region is at least 6 nucleotides.

16. The method of claim 1, wherein the ligase is T4 DNA ligase.

17. The method of claim 1, wherein the denaturing comprises applying heat to the oligonucleotide.

18. The method of claim 1, wherein the denaturing comprises contacting the oligonucleotide with a denaturing solution.

19. A method of assembling an oligonucleotide having an arbitrary sequence, the method comprising:

identifying a binary string to encode in the oligonucleotide;

a. contacting an anchor strand attached to a microelectrode array comprising a plurality of individually addressable electrodes with an oligonucleotide hairpin under conditions such that an overhang region of the oligonucleotide hairpin hybridizes to the anchor strand, the oligonucleotide hairpin comprising:

a loop region; and a stem region having an overhang side and a non-overhang side, wherein an end of the overhang side includes the overhang region of at least 3 nucleotides, an end of the non-overhang side includes a payload region with a length of 2-5 nucleotides, and the non-overhang side includes an enzyme cleavage region directly adjacent to the payload region, the enzyme cleavage region cleaved by contact with a cleavage enzyme;

b. contacting the oligonucleotide with ligase under conditions such that the ligase catalyzes formation of a phosphodiester bond between the payload region of the oligonucleotide hairpin and the anchor strand;

c. contacting the oligonucleotide with the cleavage enzyme under conditions such that the cleavage enzyme cleaves the enzyme cleavage region thereby separating the payload region from a remainder of the oligonucleotide hairpin and the payload region remains attached to the anchor strand;

d. denaturing a double-stranded structure formed from hybridization of the oligonucleotide hairpin to the anchor strand;

e. washing the oligonucleotide following the denaturing to remove the remainder of the oligonucleotide hairpin; and repeating steps a-e adding during each round an oligonucleotide hairpin that encodes in the payload region a first bit or a second bit, the oligonucleotide hairpins added in an order based on the binary string, wherein there are only four species of oligonucleotide hairpins and the oligonucleotide hairpin added in each round is selected based on a bit to be encoded and the payload region of the oligonucleotide hairpin added immediately prior so that an overhang region of the added oligonucleotide hairpin is complementary to the payload region of the oligonucleotide hairpin added immediately prior.

20. The method of claim 19, further comprises selectively activating at least one electrode in the microelectrode array to electrostatically attract the oligonucleotide hairpin to a specific location on the microelectrode array.

* * * * *